US012245825B2

United States Patent
Harris, Jr. et al.

(10) Patent No.: US 12,245,825 B2
(45) Date of Patent: Mar. 11, 2025

(54) SYSTEMS AND METHODS OF USING PHOTOGRAMMETRY FOR INTRAOPERATIVELY ALIGNING SURGICAL ELEMENTS

(71) Applicant: MicroPort Orthopedics Holdings Inc., Arlington, TN (US)

(72) Inventors: Brian R. Harris, Jr., Cordova, TN (US); Fred W. Bowman, Germantown, TN (US)

(73) Assignee: MicroPort Orthopedics Holdings Inc., Arlington, TN (US)

( * ) Notice: Subject to any disclaimer, the term of this patent is extended or adjusted under 35 U.S.C. 154(b) by 161 days.

(21) Appl. No.: 17/936,130

(22) Filed: Sep. 28, 2022

(65) Prior Publication Data

US 2023/0094903 A1    Mar. 30, 2023

Related U.S. Application Data

(60) Provisional application No. 63/250,906, filed on Sep. 30, 2021.

(51) Int. Cl.
*A61B 34/20* (2016.01)
*A61B 90/00* (2016.01)
(Continued)

(52) U.S. Cl.
CPC ............ *A61B 34/20* (2016.02); *A61F 2/4607* (2013.01); *A61F 2/4609* (2013.01); *G06T 7/60* (2013.01);
(Continued)

(58) Field of Classification Search
CPC ..... A61B 34/20; A61B 2090/373; G06T 7/70; G06T 7/60; G06T 2207/10121;
(Continued)

(56) References Cited

U.S. PATENT DOCUMENTS 6,891,518 B2    5/2005 Sauer et al.
6,919,867 B2    7/2005 Sauer
(Continued)

FOREIGN PATENT DOCUMENTS

CN    102599960    8/2015
CN    105266897    1/2016
(Continued)

OTHER PUBLICATIONS

S.Hosseinian, H. Arefi, Photogrammetry in 3D Modelling of Human Bone Structures From Radiographs, International Archives of the Photogrammetry, Remote Sensing and Spatial Information Sciences, vol. XLII-2/W4, 2017 2nd International ISPRS Workshop on PSBB, May 15-17, 2017, Moscow, Russia.
(Continued)

*Primary Examiner* — Sean A Frith
(74) *Attorney, Agent, or Firm* — Robert J. Hornung

(57) ABSTRACT

Systems and methods for ascertaining a position of an orthopedic element in space comprising: capturing a first and second images of an orthopedic element in different reference frames using a radiographic imaging technique, detecting spatial data defining anatomical landmarks on or in the orthopedic element using a deep learning network, applying a mask to the orthopedic element defined by an anatomical landmark, projecting the spatial data from the first image and the second image to define volume data, applying the deep learning network to the volume data to generate a reconstructed three-dimensional model of the orthopedic element; and mapping the three-dimensional model of the orthopedic element to the spatial data to determine the position of the three-dimensional model of the orthopedic element in three-dimensional space.

17 Claims, 15 Drawing Sheets

(51) Int. Cl.
*A61F 2/46* (2006.01)
*G06T 7/60* (2017.01)
*G06T 7/70* (2017.01)

(52) U.S. Cl.
CPC .......... *G06T 7/70* (2017.01); *A61B 2090/373* (2016.02); *A61F 2002/4668* (2013.01); *G06T 2207/10121* (2013.01); *G06T 2207/20084* (2013.01); *G06T 2207/30008* (2013.01); *G06T 2207/30052* (2013.01)

(58) Field of Classification Search
CPC . G06T 2207/20084; G06T 2207/30008; G06T 2207/30052; A61F 2/4607; A61F 2/4609; A61F 2002/4668
See application file for complete search history.

(56) References Cited

U.S. PATENT DOCUMENTS

| | | | |
|---|---|---|---|
| 7,511,736 | B2 | 3/2009 | Benton |
| 7,618,451 | B2 | 11/2009 | Berez et al. |
| 7,771,436 | B2 | 8/2010 | Moctezuma De La Barrera et al. |
| 7,774,044 | B2 | 8/2010 | Sauer et al. |
| 7,806,896 | B1 | 10/2010 | Bonutti |
| 8,485,038 | B2 | 7/2013 | Sengupta et al. |
| 8,543,338 | B2 | 9/2013 | Bronstein et al. |
| 8,634,897 | B2 | 1/2014 | Simon et al. |
| 8,657,809 | B2 | 2/2014 | Schoepp |
| 8,842,893 | B2 | 9/2014 | Teichman et al. |
| 8,963,957 | B2 | 2/2015 | Skarulis |
| 9,089,342 | B2 | 7/2015 | Carroll et al. |
| 9,439,622 | B2 | 9/2016 | Case et al. |
| 9,547,940 | B1 | 1/2017 | Sun et al. |
| 9,610,056 | B2 | 4/2017 | Lavallee et al. |
| 9,681,925 | B2 | 6/2017 | Azar et al. |
| 9,901,463 | B2 | 2/2018 | Mahfouz |
| 10,166,109 | B2 | 1/2019 | Ferko |
| 10,258,426 | B2 | 4/2019 | Silva et al. |
| 10,510,155 | B1 | 12/2019 | Islam et al. |
| 10,722,310 | B2 | 7/2020 | Luby |
| 10,940,021 | B2 | 3/2021 | Mahfouz |
| 11,076,872 | B2 | 8/2021 | Wilkinson |
| 11,423,603 | B2 | 8/2022 | Sutton et al. |
| 11,439,469 | B2 | 9/2022 | Poltaretskyi et al. |
| 2008/0114370 | A1 | 5/2008 | Schoenefeld |
| 2008/0167550 | A1 | 7/2008 | Weiser et al. |
| 2009/0306679 | A1 | 12/2009 | Murphy |
| 2011/0071533 | A1 | 3/2011 | Metzger et al. |
| 2011/0236868 | A1 | 9/2011 | Brohstein et al. |
| 2012/0065640 | A1 | 3/2012 | Metzger et al. |
| 2013/0060146 | A1 | 3/2013 | Yang et al. |
| 2013/0117377 | A1 | 5/2013 | Miller |
| 2013/0165941 | A1 | 6/2013 | Murphy |
| 2013/0310838 | A1 | 11/2013 | Kurtz |
| 2014/0013565 | A1 | 1/2014 | MacDonald et al. |
| 2014/0013566 | A1 | 1/2014 | MacDonald |
| 2016/0008143 | A1 | 1/2016 | Mahfouz |
| 2016/0026253 | A1 | 1/2016 | Bradski et al. |
| 2016/0228193 | A1 | 8/2016 | Moctezuma de la Barrera et al. |
| 2018/0168740 | A1 | 6/2018 | Ryan et al. |
| 2018/0177600 | A1 | 6/2018 | Karlsson et al. |
| 2018/0185100 | A1 | 7/2018 | Weinstein et al. |
| 2019/0008532 | A1 | 1/2019 | Fitz et al. |
| 2019/0262078 | A1 | 8/2019 | Lang |
| 2019/0380792 | A1* | 12/2019 | Poltaretskyi ............ G06F 30/20 |
| 2020/0138522 | A1 | 5/2020 | Tikka |
| 2020/0197107 | A1* | 6/2020 | Ryan .................. A61B 90/361 |
| 2020/0275976 | A1* | 9/2020 | McKinnon ............ A61B 90/37 |
| 2020/0281742 | A1* | 9/2020 | Wu ...................... A61F 2/4607 |
| 2020/0375666 | A1 | 12/2020 | Murphy |
| 2020/0405399 | A1* | 12/2020 | Steinberg .................. G06T 7/33 |
| 2022/0096245 | A1 | 3/2022 | Sun et al. |

FOREIGN PATENT DOCUMENTS

| | | |
|---|---|---|
| WO | 2012154534 | 11/2012 |
| WO | 2014120909 | 8/2014 |
| WO | 2016078919 | 5/2016 |
| WO | 2017066373 | 4/2017 |
| WO | 2018078017 | 4/2017 |
| WO | 2017200444 | 11/2017 |
| WO | 2021245093 | 12/2021 |

OTHER PUBLICATIONS

Fausto Milletari, et. al., V-Net: Fully Convolutional Neural Networks for Volumetric Medical Image Segmentation., arXiv:1606.04797v1 [cs.CV] Jun. 15, 2016.

J. C. K. Chow, Modelling Errors in X-Ray Fluoroscopic Imaging Systems Using Photogrammetric Bundle Adjustment With a Data-Driven Self-Calibration Approach, The International Archives of the Photogrammetry, Remote Sensing and Spatial Information Sciences, vol. XLII-1, 2018 ISPRS TC I Mid-term Symposium "Innovative Sensing—From Sensors to Methods and Applications", Oct. 10-12, 2018, Karlsruhe, Germany.

Dr. F. G. Lippert III, M.D., An Analytical Approach to X-Ray Photogrammetry, Photogrammetric Engineering and Remote Sensing, vol. 43, No. 12, Dec. 1977, pp. 1503-1510. S. A. Veress, Ds.C., University of Washington, Seattle, WA 98195.

Avi-Ben-Cohen, Retinal layers segmentation using Fully Convolutional Network in OCT images.

Yoni Kasten, End-To-End Convolutional Neural Network for 3D Reconstruction of Knee Bones From Bi-Planar X-Ray Images, arXiv:2004.00871v2 [eess.IV] Aug. 12, 2020.

Ilya Kovler, Haptic computer-assisted patient-specific preoperative planning for orthopedic fractures surgery, Int J CARS DOI 10.1007/s11548-015-1162-9.

Sandor A. Veress, X-Ray Photogrammetry, State of the Art, University of Washington Seattle, WA 98195 United States IPRS Commission V.

Zimmer Biomet, Image Acquisition Protocol for X-PSI™ Knee System, 2018.

Vincent Masse, Raju S. & Ghate, "Using Standard X-ray Images to Create 3D Digital Bone Models and Patient-Matched Guides for Aiding Implant Positioning and Sizing in Total Knee Arthroplasty," Computer Assisted Surgery, Mar. 15, 2021, 36:1, 31-40.

Tanguy Roudaut, Partial European Search Report and Written Opinion for EP app, No. 22182089, Feb. 23, 2023, Munich, Germany.

Thomas, Shane, International Search Report for PCT/US22/77111, Dec. 28, 2022, USPTO as ISA, Alexandria, Virginia, USA.

Thomas, Shane, Written Opinion of the International Searching Authority for PCT/US22/77111, Dec. 28, 2022, USPTO as ISA, Alexandria, Virginia, USA.

Matos, Taina, International Search Report for PCT/US22/77133, Dec. 8, 2022, USPTO as ISA, Alexandria, Virginia, USA.

Matos, Taina, Written Opinion of the International Searching Authority for PCT/US22/77133, Dec. 8, 2022, USPTO as ISA, Alexandria, Virginia, USA.

Thomas, Shane, International Search Report for PCT/US22/73868, Oct. 11, 2022, USPTO as ISA, Alexandria, Virginia, USA.

Thomas, Shane, Written Opinion of the International Searching Authority for PCT/US22/73868, Oct. 11, 2022, USPTO as ISA, Alexandria, Virginia, USA.

Yilmaz, Ozgun, Supplementary European Search Report (art. 153(7) EPC) and European Search Opinion, Oct. 4, 2024, Munich, Germany.

A Uneri et. al., "Known-component 3D-2D registration for quality assurance of spine surgery pedicle screw placement," Physics in Medicen & Biology, 2015, vol. 50, pp. 8007-8024, United Kingdom.

* cited by examiner

SYSTEMS AND METHODS OF USING PHOTOGRAMMETRY FOR INTRAOPERATIVELY ALIGNING SURGICAL ELEMENTS

REFERENCE TO RELATED APPLICATION

This application claims the benefit of priority to U.S. Provisional Application No. 63/250,906 filed on Sep. 30, 2021. The disclosure of this related application is hereby incorporated into this disclosure in its entirety.

BACKGROUND OF THE INVENTION

1. Technical Field

The present disclosure relates generally to the field of orthopedic joint replacement surgeries and more particularly to using photogrammetry and three-dimensional ("3D") reconstruction techniques to aid surgeons and technicians in planning and executing orthopedic surgeries.

2. Related Art

An objective of hip replacement surgeries is to restore the natural alignment and range of motion of the patient's pre-diseased hip. However, this objective can be difficult to achieve in practice, because hips comprise not only the articulating bones but also a variety of soft tissue, including cartilage, muscle, ligaments, and tendons. In all hip arthroplasties, and especially in minimally invasive hip arthroplasties, the presence of these soft tissues can severely limit the surgeon's visual field. This problem is even more pronounced in patients with a high body mass index.

In a hip arthroplasty, the pelvis itself is enclosed nearly entirely in soft tissue. In a minimally invasive procedure, the main incision eventually exposes the junction of the acetabulum and the proximal femoral head, but this main incision typically directs the surgeon's view across the margin (i.e., perimeter) of the acetabulum. A portal incision extending through one or more quadriceps muscles of the operative leg may align with the concave face of the acetabulum, but the proximal end of the femur must be dislodged and rotated away from the acetabulum to expose this view.

To complicate matters further, the visual field of the operative area through a portal incision is generally much more limited than the visual field through the main incision. An endoscopic camera may be placed through the portal incision to capture an image of the concave acetabular surface, but the concave surface of the acetabulum lacks boney markers (i.e., landmarks) that can be used to indicate the position of the acetabulum and pelvis reliably. Furthermore, any movement of the femur will likely translate to the pelvis through the connective soft tissue, thereby undermining the usefulness of any images captured by the endoscopic camera. Use of an endoscopic camera therefore would needlessly prolong the procedure and have very limited effectiveness in accurately reflecting the position of the acetabulum relative to the proximal femur.

Artificial hip implants typically comprise an acetabular shell, which the surgeon places into a reamed acetabulum of the hip. The acetabular shell may house a liner that functions essentially as a bearing with the generally spherically shaped head of the femoral component. The femoral component generally comprises a stem, a neck, and the head. When installed, the stem is inserted into a resected and reamed proximal end of the femur. The neck connects a proximal end of the stem to the head. The head in turn, is placed in the artificial acetabular cup, and commonly is disposed against the liner of the acetabular cup.

Because the surgeon's field of view of the surgical area is so often obstructed by soft tissue, surgeons have relied upon external indicia in the past to try to estimate the proper alignment of the acetabular cup in the acetabulum. US. Pat. Pub. No. 2013/0165941 to Murphy is one such example. Other providers offered positioning guides that comprised external horizontal and vertical positioning bars designed to resemble the axes of a Cartesian plane. To try to achieve an abduction angle of the acetabular cup of about 40 degrees ("°") to about 45°, the surgeon would position the placement guide roughly diagonally to the body longitudinal axis of the patient (i.e., an imaginary center line of the body that extends from the patient's head to groin), such that a horizontal positioning bar would be disposed roughly parallel to the body longitudinal axis. To attempt to achieve an anteversion angle of about 10° to about 15°, the surgeon would lift the positioning device slightly along the vertical positioning bar relative to the body longitudinal axis.

These external indicia did not account for the patient's specific anatomy, nor did they account for movement of the pelvis relative to these indicia. For example, it is entirely possible that when a given patient is lying supine, the patient's left acetabulum may be positioned slightly lower than the patient's right acetabulum. Furthermore, many hip arthroplasty procedures require repositioning of the patient to make certain incisions or to access certain portions of the surgical area. As noted above, movement of the femur is likely to translate to the pelvis through the soft tissue. Given the need to reposition the patient multiple times throughout a standard hip arthroplasty, it is unlikely that the pelvis will always be located within the suggested use parameters for existing acetabular cup positioning guides that rely upon external indicia.

Properly aligning, sizing, and installing the femoral component is even more difficult, given that allowing the surgeon to have a direct line of sight to the proximal femur requires dislocating (and therefore misaligning) the proximal femur from the acetabulum (or the acetabular cup as the case may be). As a result, many surgeons have relied upon sound and feel to approximate acceptable femoral stem placement. Both the femoral stem and the acetabular cup are impacted into their respective bones. A femoral stem that is too large could easily fracture the proximal femur. A femoral stem that is too small may subside into the intramedullary canal of the femur over time as the result of normal use. Subsidence can shorten the patient's gait and place undue pressure on the neck, head, and portions of the liner, thereby accelerating wear.

Additionally, even if the acetabular cup is placed in the reamed acetabulum at desirable angles of abduction and anteversion, and even if an adequately sized femoral stem is seated in the proximal femur, the position of the femoral component relative to the acetabular cup was previously not knowable using conventional technologies. Intraoperative fluoroscopy could be used to generate a two-dimensional ("2D") image of the femoral component relative to the acetabular component, but the fluoroscopic image lacked sufficient 3D information to ensure accurate alignment. For example, with classic fluoroscopy, the pelvic tilt was unknown. As such, the orientation of any boney landmarks on the pelvis was also unknown. Without being able to determine the orientation of the pelvis with precision, it was not possible to use fluoroscopy alone to accurately calculate the position of the natural pre-diseased joint line. Furthermore, prolonged use of fluoroscopy subjects the patient to excessive radiation.

Improper alignment of the femoral component's head relative to the acetabular cup could result in a shortening of the operative leg relative to the contralateral leg, dislocation of the head relative to the acetabular cup, and increased force loading on one part of the acetabular cup, liner, head, or neck (which thereby increases the rate of wear and reduced implant longevity). Any of these shortcomings can contribute to patient discomfort.

As a result, surgeons have had to remain content operating within a fairly large margin of error for acetabular cup placement. Despite the available tools and procedures, aligning a reconstructed hip in a typical hip arthroplasty is based on experience, educated guesses, and chance. This problem can be particularly pronounced in minimally invasive hip arthroplasties in part because the surgeon's field of view is so restricted.

SUMMARY OF THE INVENTION

Accordingly, there is a long felt but unresolved need to augment preoperative and intraoperative imaging technologies to accurately model the operative joint anatomy and artificial endoprosthetic implant when planning and executing hip arthroplasties.

The problems of limited surgeon visualization of the operative area in minimally invasive surgeries using currently available preoperative or intraoperative tools and techniques and the attendant problems of misalignment that such lack of visualization can cause can be mitigated by exemplary systems or methods for ascertaining a position of an orthopedic element in space comprising: using a deep learning network to identify an orthopedic element and a component of an endoprosthetic implant and to map the identified orthopedic element and the identified component of the endoprosthetic implant to spatial data from an input of at least two separate two-dimensional ("2D") input images of a subject orthopedic element, wherein the first image of the at least two separate 2D input images is captured from a first transverse position, and wherein the second image of the at least two separate 2D input images is captured from a second transverse position offset from the first transverse position by an offset angle.

In exemplary embodiments, the input images can be radiographic images. Without being bound by theory, radiographs may be desirable because radiographs allow for in-vivo analysis that can account for external summation of passive soft tissue structures and dynamic forces occurring around the hip, including the effect of ligamentous restraints, load-bearing forces, and muscle activity.

Without being bound by theory, it is contemplated that by mapping the model of an orthopedic element and a model of a component of an endoprosthetic implant to spatial data, the position of the mapped and modeled orthopedic element can be calculated relative to the mapped and modeled implant component. If this system is applied to two or more orthopedic elements and two or more components of the endoprosthetic implant, the components of the endoprosthetic implants can be desirably implanted into their respective orthopedic elements at desirable positions and the respective endoprosthetic implant components can be desirably aligned relative to one another.

It is further contemplated that certain exemplary systems and methods described herein can be configured to accurately predict the desired size of an implant component relative to the adjacent orthopedic element.

It is still further contemplated that certain exemplary systems and methods described herein can be configured to accurately orient the placement of an endoprosthetic implant component relative to an orthopedic element in which the endoprosthetic implant component will be implanted.

BRIEF DESCRIPTION OF THE DRAWINGS

The foregoing will be apparent from the following more particular description of exemplary embodiments of the disclosure, as illustrated in the accompanying drawings. The drawings are not necessarily to scale, with emphasis instead being placed upon illustrating the disclosed embodiments.

FIG. 3 depicts the principle of the abduction angle and the anteversion angle.

DETAILED DESCRIPTION OF THE PREFERRED EMBODIMENTS

Figure 1:
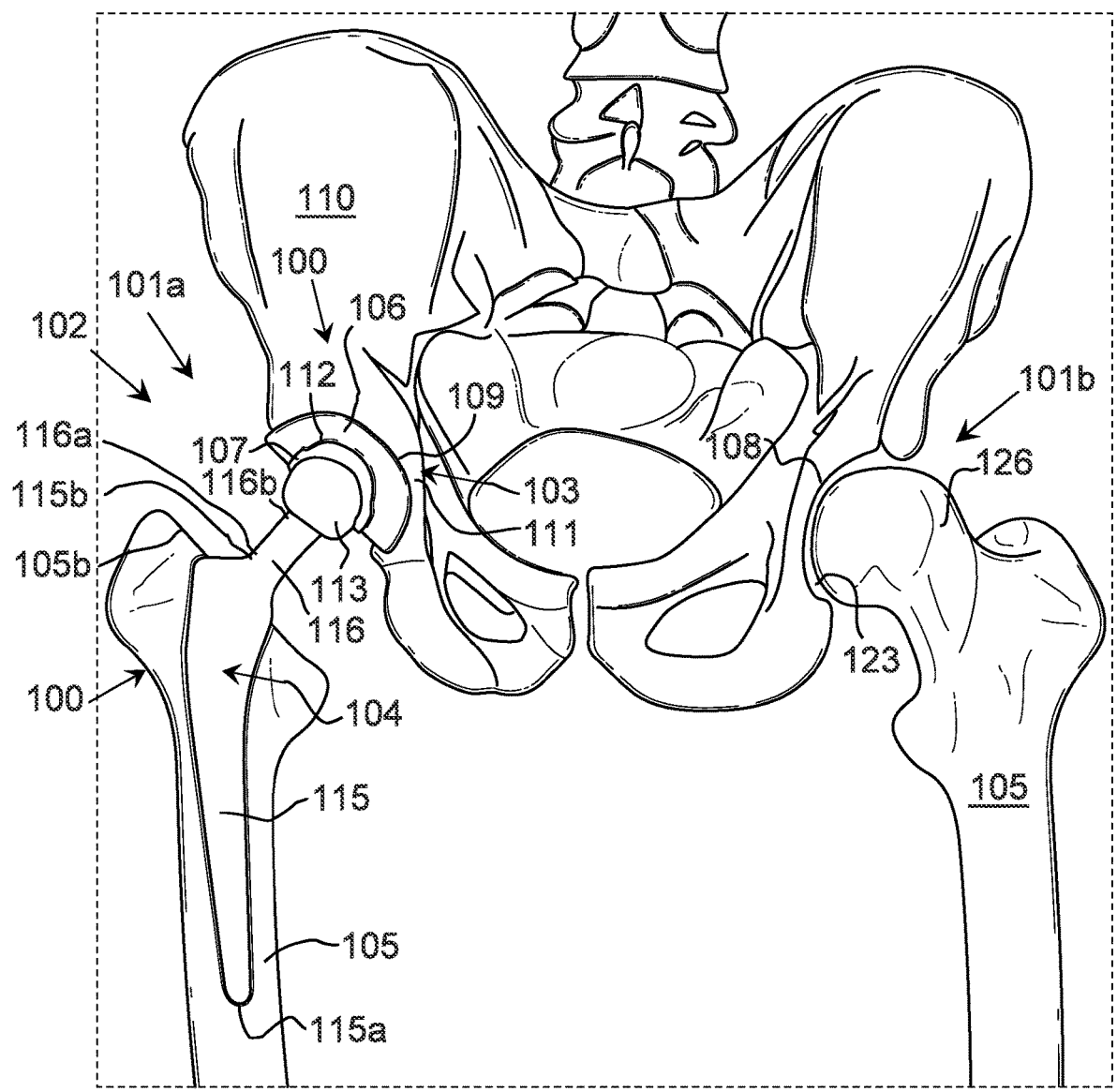
FIG. 1 is a simplified X-ray view of the front of a patient depicting an example endoprosthetic hip implant in the right hip and a natural left hip.

The following detailed description of the preferred embodiments is presented only for illustrative and descriptive purposes and is not intended to be exhaustive or to limit the scope and spirit of the invention. The embodiments were selected and described to best explain the principles of the invention and its practical application. One of ordinary skill in the art will recognize that many variations can be made to the invention disclosed in this specification without departing from the scope and spirit of the invention.

Similar reference characters indicate corresponding parts throughout the several views unless otherwise stated. Although the drawings represent embodiments of various features and components according to the present disclosure, the drawings are not necessarily to scale and certain features may be exaggerated to better illustrate embodiments of the present disclosure, and such exemplifications are not to be construed as limiting the scope of the present disclosure.

Except as otherwise expressly stated herein, the following rules of interpretation apply to this specification: (a) all words used herein shall be construed to be of such gender or number (singular or plural) as such circumstances require; (b) the singular terms "a," "an," and "the," as used in the specification and the appended claims include plural references unless the context clearly dictates otherwise; (c) the antecedent term "about" applied to a recited range or value denotes an approximation with the deviation in the range or values known or expected in the art from the measurements; (d) the words, "herein," "hereby," "hereto," "hereinbefore," and "hereinafter," and words of similar import, refer to this specification in its entirety and not to any particular paragraph, claim, or other subdivision, unless otherwise specified; (e) descriptive headings are for convenience only and shall not control or affect the meaning of construction of part of the specification; and (f) "or" and "any" are not exclusive and "include" and "including" are not limiting. Further, the terms, "comprising," "having," "including," and "containing" are to be construed as open-ended terms (i.e., meaning "including but not limited to").

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments, whether explicitly described.

To the extent necessary to provide descriptive support, the subject matter and/or text of the appended claims are incorporated herein by reference in their entirety.

Recitation of ranges of values herein are merely intended to serve as a shorthand method of referring individually to each separate value falling within the range of any subranges there between, unless otherwise clearly indicated herein. Each separate value within a recited range is incorporated into the specification or claims as if each separate value were individually recited herein. Where a specific range of values is provided, it is understood that each intervening value, to the tenth or less of the unit of the lower limit between the upper and lower limit of that range and any other stated or intervening value in that stated range of sub range thereof, is included herein unless the context clearly dictates otherwise. All subranges are also included. The upper and lower limits of these smaller ranges are also included therein, subject to any specifically and expressly excluded limit in the stated range.

It should be noted that some of the terms used herein are relative terms. For example, the terms, "upper" and, "lower" are relative to each other in location, i.e., an upper component is located at a higher elevation than a lower component in each orientation, but these terms can change if the orientation is flipped The terms, "horizontal" and "vertical" are used to indicate direction relative to an absolute reference, i.e., ground level. However, these terms should not be construed to require structure to be absolutely parallel or absolutely perpendicular to each other. For example, a first vertical structure and a second vertical structure are not necessarily parallel to each other. The terms, "top" and "bottom" or "base" are used to refer to locations or surfaces where the top is always higher than the bottom or base relative to an absolute reference, i.e., the surface of the Earth. The terms, "upwards" and "downwards" are also relative to an absolute reference; an upwards flow is always against the gravity of the Earth.

Orthopedic procedures frequently involve operating on a patient's joint. It will be understood that a joint typically comprises a multitude of orthopedic elements. It will further be appreciated that the exemplary methods and systems described herein can be applied to a variety of orthopedic elements. The examples described with reference to FIGS. 1-4, 9A-9C, and 11 relate to a hip joint for illustration purposes. It will be appreciated that the "orthopedic element" 100 referenced throughout this disclosure is not limited to the anatomy of a hip joint, but can include any skeletal structure or associated soft tissue, such as tendons, ligaments, cartilage, and muscle. A non-limiting list of example of skeletal orthopedic elements 100 includes any partial or complete bone from a body, including but not limited to a femur, tibia, pelvis, vertebra, humerus, ulna, radius, scapula, skull, fibula, clavicle, mandible, rib, carpal, metacarpal, tarsal, metatarsal, phalange, or any associated tendon, ligament, skin, cartilage, or muscle. It will be appreciated that an example operative area 170 can comprise several subject orthopedic elements 100. Likewise, it will be appreciated that an operative area 170 is not limited to the hip operative area that is used as the primary example herein, but rather can return to any area of a body that is the target of a surgical operation. This may include by non-limiting example, the knee, ankle, spine, shoulder, wrist, hand, foot, mandible, skull, rib, and phalanges.

FIG. 1 is a simplified representation of an X-ray image of the front of an example patient's pelvis 110. Both patient's right hip joint 101a and left hip joint 101b are shown. Both example hip joints 101a, 101b comprise a number of orthopedic elements 100, including a femur 105, an acetabulum (see 108 and 111) of the pelvis 110, and connective tissues. The depicted right hip joint 101a (i.e., the hip joint on the patient's right side, which is depicted on the left side of the page) shows an example endoprosthetic hip implant 102 that has been surgically installed into the patient. The depicted left hip joint 101b shows an example natural hip joint for comparison.

Referring to the depicted right hip joint 101a, the example endoprosthetic hip implant 102 generally comprises an acetabular component 103 and a femoral component 104. It will be appreciated that endoprosthetic implants in general can comprise multiple components (e.g., an acetabular component 103 and a femoral component 104); these components in turn may be comprised of multiple subcomponents. In the depicted example, the acetabular component 103 typically comprises a generally hemispherical acetabular shell 106 and an inner liner 107. The acetabular shell 106 is typically made from cobalt chrome, titanium, or other biocompatible metal. The inner liner 107 is typically made from a ceramic, metal, polymer, or other biocompatible material having a low coefficient of friction and a low wear rate.

To prepare the native acetabulum (see 108) for the installation of the acetabular shell 106, the surgeon first uses a hemispherical reamer to create a generally concave surface in the patient's native acetabulum 108 to define a "reamed acetabulum" 111. The reamed acetabulum 111 is generally complementary to the convex outer surface 109 of the acetabular shell 106. The outer surface 109 of the acetabular shell 106 is usually roughened to facilitate engagement to the reamed acetabulum 111. The roughened surface is also thought to promote osteogenesis into the spaces of the roughened surface, thereby increasing the strength of the bond over time.

The inner liner 107 typically sits adjacent to an inner concave surface 112 of the acetabular shell 106, when the inner liner 107 is in its assembled and installed configuration. The inner liner 107 generally functions as a bearing against which the femoral head 113 of the femoral component 104 articulates once installed.

The femoral component 104 typically comprises the femoral stem 115 having a distal stem end 115a that is distally disposed from a proximal stem end 115b, a neck 116 having a distal neck end 116a engaging the proximal stem end 115b. The neck 116 extends to a head end 116b. A generally spherically shaped artificial femoral head 113 is disposed at the head end 116b of the neck 116 in an assembled configuration. In certain exemplary embodiments, the neck 116 can be selectively detachable from the proximal stem end 115b. Such selectively detachable necks 116 can be known as "modular necks."

It will be appreciated that the acetabular component 103 and the femoral component 104, and the subcomponents that comprise the acetabular component 103 or the femoral component 104 (e.g., the acetabular shell 106, inner liner 107, any fixation fasteners, the femoral stem 115, artificial femoral head 113, etc.) are typically provided in one or more surgical kits in an uninstalled and unassembled configuration. In an uninstalled and unassembled configuration, a component or subcomponent does not physically engage another component or subcomponent. Stated another way force is not directly transferred from one component or subcomponent to another component or subcomponent in an uninstalled and unassembled configuration. In as assembled configuration, the components or subcomponents physically contact one another and force can be transferred through two or more proximally disposed components or subcomponents. In an assembled and installed configuration, the components or subcomponents are in the assembled configuration and are also surgically implanted into the patient.

For comparison, the depicted left hip joint 101b shows the natural femoral head 126 at the proximal end of the femur 105. The natural femoral head 126 is disposed within the natural acetabulum 108 of the pelvis 110. Articular cartilage 123 coats the articular surface of both the healthy femoral head 126 and the healthy acetabulum 108.

There are many surgical approaches to a typical hip arthroplasty, but most minimally invasive procedures begin with the surgeon making a six to eight centimeters ("cm") incision in the operative leg that is radially proximate to the hip joint capsule. Various muscles and tendons are then retracted with surgical instruments to eventually expose the joint capsule. The capsule is then pierced, and the surgeon dislocates the natural femoral head 126 from the natural acetabulum 108.

Femoral preparation involves resecting and removing the natural femoral head 126 from the femur 105. After the natural femoral head 126 is removed, the surgeon may then drill a canal into the intramedullary space of newly exposed proximal end 105b of the femur 105. The surgeon may then use a femoral broach to expand the space in the intramedullary canal needed to accommodate the femoral stem 115. Trial stems may be used to test the sizing and positioning of the femoral component 104. Trial components generally have the same dimensions as the actual implant components, but the trial components are designed to be installed and removed more easily.

Acetabular preparation involves reaming the natural acetabulum 108 to define a reamed acetabulum 111. The goal is to create a generally uniform hemispherical space that is complementary to the generally hemispherical outer surface 109 of the acetabular shell 106. Trial acetabular components can be used to try to test the alignment of the acetabular component 103 relative to the femoral component 104, but visibility is limited and the nature of the procedure typically does not permit exhaustive testing of the alignment. Furthermore, because visibility is limited, there is a chance that the actual implant components 103, 104 will not be oriented in exactly the same way as the trial components.

Figure 2:
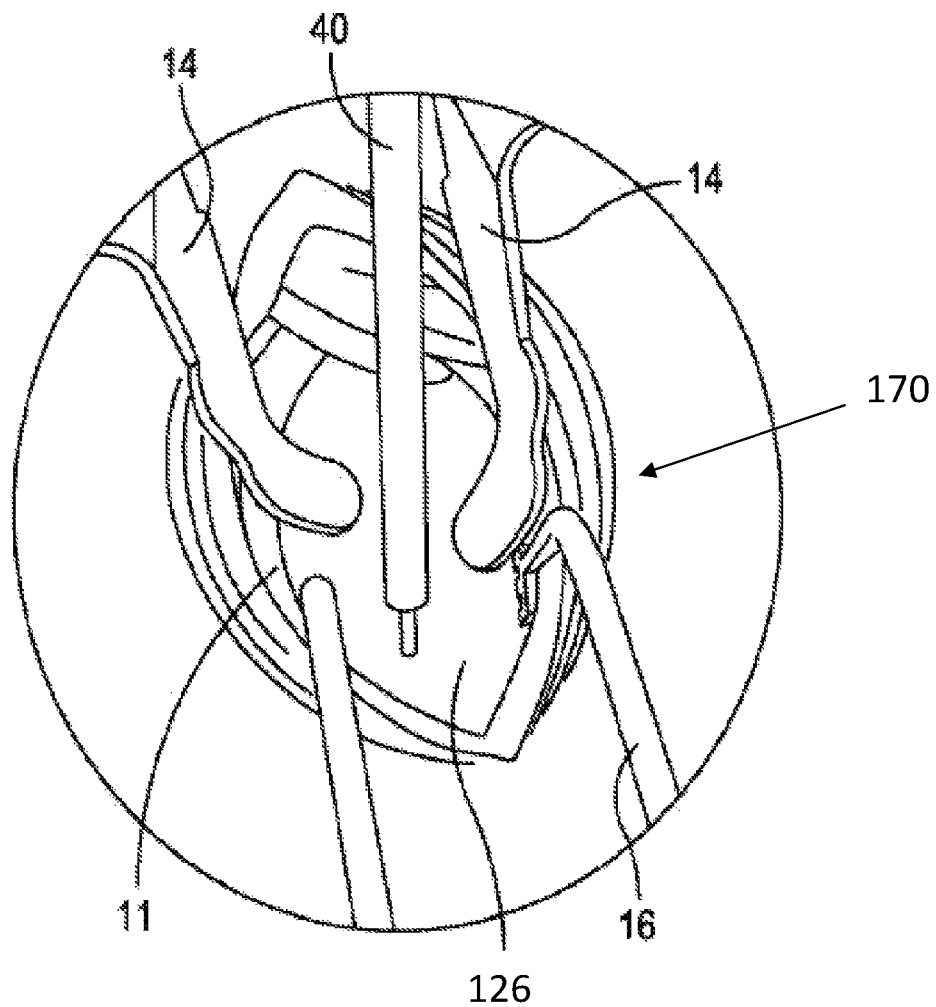
FIG. 2 illustrates a surgeon's typical field of view in a minimally invasive hip arthroplasty.

It will be appreciated that there are a variety of surgical approaches for a typical total hip arthroplasty (e.g., some surgeons choose to approach the hip posteriorly, while other choose to approach the hip joint laterally or anteriorly). FIG. 2 illustrates and exemplifies a surgeon's typical field of view of a typical hip arthroplasty operative area 170 through the main incision. Several retractors 14, 16 (which can include a Hohmann retractor or a Cobb elevator in some procedures) are used to retract the fascia 11 that is disposed between the area of the initial incision and the hip joint capsule. An electrocautery instrument 40 can be used to resect and cauterize tissue and to prevent excessive bleeding. The natural femoral head 126 is also shown for reference.

FIG. 2 illustrates how the six to eight cm main incision of the operative area 170, the location of the hip joint (see 101a, 101b) relative to the point of incision, and the presence of typical surgical instrumentation (e.g., retractors 14, 16, mallets, broaches, reamers, pins, implant components, etc.) can significantly interfere with the surgeon's already limited field of view. This problem, which can be exacerbated by trying to align the acetabular component 103 and the femoral component 104 of the endoprosthetic hip implant 102 relative to external indicia that are divorced from the orientation of the target's implantation anatomy (e.g., the reamed acetabulum 111 or the resected proximal femur 105 in this hip example), can lead to inaccurate alignment of the implant components 103, 104 relative to the bones into which they are implanted, and relative to each other. This in turn can contribute to the risk of implant dislocation, non-optimal force distribution, faster wear, failure of the implant, altered gait, general patient discomfort, and the need for further revision surgeries which suffer from the same limitations.

Figure 3:
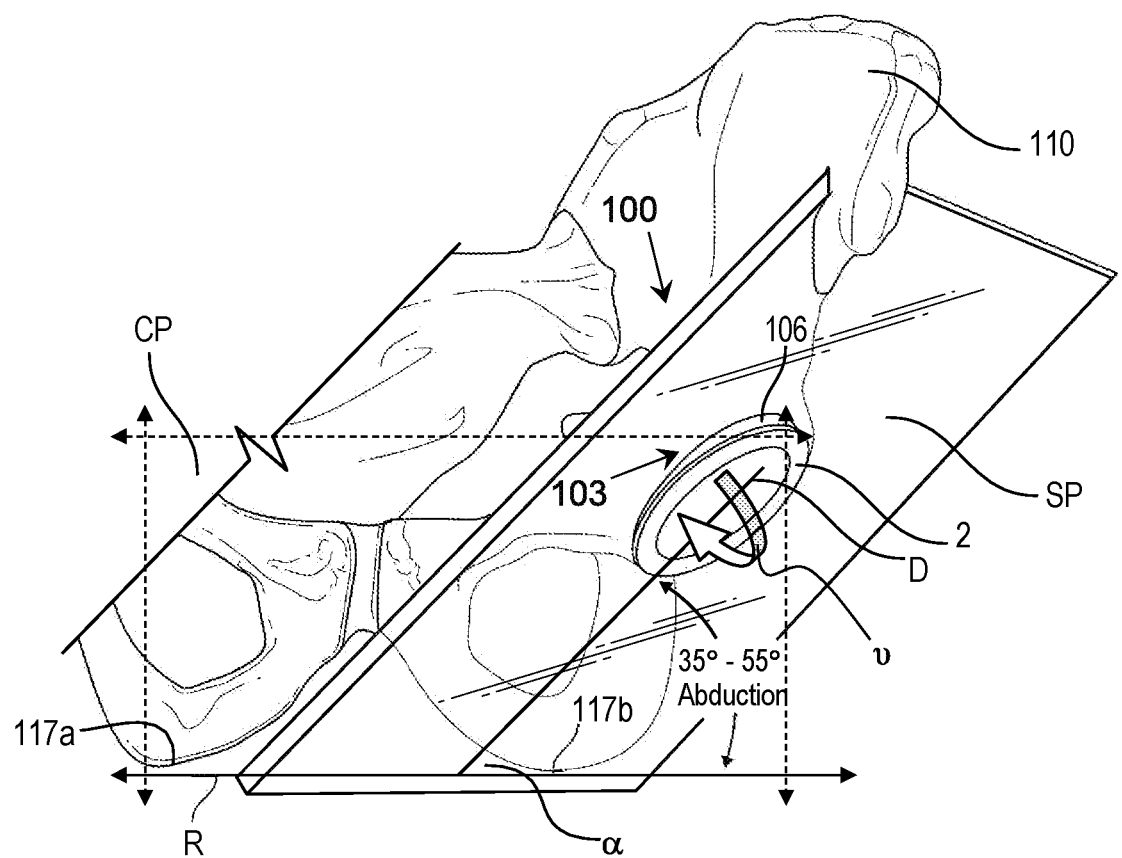
FIG. 3 is a perspective view of an example acetabular component disposed in a reamed acetabulum.

FIG. 3 is a perspective view of an example acetabular component 103 disposed in a reamed acetabulum 111. Although the abduction angle $\alpha$ and the anteversion angle $v$ are depicted with reference to the acetabular component 103, it will be appreciated that the femoral component 104 is also disposed at an abduction angle $\alpha$ and an anteversion angle $v$ in the proximal femur 105. The abduction angle $\alpha$ and an anteversion angle $v$ of a component of an endoprosthetic implant (e.g., the acetabular component 103 and the femoral component 104) relative to the orthopedic element (e.g., the pelvis 110 and 105 proximal femur respectively) into which the component of the endoprosthetic implant is implanted can be calculated and determined by those having ordinary skill in the art.

It will be appreciated that a "component of an endoprosthetic implant" can vary based upon the type of endoprosthetic implant and the type of operative area 170. For example, when the operative area 170 is a hip, a "component of an endoprosthetic implant" can be selected from a group comprising an acetabular component 103, a femoral component 104, a trial construct, instrumentation used in or to facilitate the installation of the endoprosthetic implant or trial implants in the patient in the installed position, or combinations thereof. In embodiments where the operative area 170 is a knee, a "component of an endoprosthetic implant" can be a femoral component of an endoprosthetic knee implant, a tibial component of an endoprosthetic knee implant, a trial construct, instrumentation used in or to facilitate the installation of the endoprosthetic implant or trial implants in the patient in the installed position, or combinations thereof.

To illustrate the principle of the abduction angle α of the acetabular component 103 relative to the pelvis 110 more clearly, the soft tissue has been omitted in FIG. 3. The abduction angle α can be measured by several ways known by those having ordinary skill in the art. One such way of visualizing the abduction angle α of the acetabular component 103 is by drawing a diameter line D extending through the diameter of the rim of the acetabular shell 106 on a coronal plane CP relative to a generally horizontal medial-lateral reference line R that is co-planar with the coronal plane CP of the diameter line D. In FIG. 3, the reference line R is shown connecting the distalmost portions of the right and left ischia 117a, 117b; however, it will be appreciated that other reference markers may be used provided that the reference line R extends horizontally, medial-laterally, and co-planarly coronally with the diameter line D.

A shell plane SP is also shown extending coplanar through the rim 2 of the acetabular shell 106. Aligning the acetabular shell 106 in three dimensional space can be thought to involve the selection of the proper compound angle, the compound angle comprising the abduction angle α and the anteversion angle v. The shell plane SP is shown to depict the concept of acetabular shell alignment in three dimensions more clearly. It will be appreciated that the diameter line D, coronal plane CP, shell plane SP, and the medial-lateral reference line R are geometric reference elements that are depicted to illustrate the concept of the abduction angle α and acetabular alignment generally. These geometric reference elements need not be visible in practice.

Many acetabular shells 106 are designed to be installed in the reamed acetabulum 111 at an abduction angle α of about 30° to about 50°. However, this wide margin underscores the difficulty in properly aligning an acetabular shell 106 in the reamed acetabulum 111 using conventional methods. Furthermore, the general guidance of having an abduction angle α of about 30° to about 50° does not account for variability in particular patients.

FIG. 3 also illustrates the concept of the anteversion angle v. The anteversion angle v can be calculated by several ways known to those having ordinary skill in the art. One such way to visualize the anteversion angle v of the acetabular shell 106 is to imagine the anteversion angle v as the rotation of the acetabular shell 106 around the center diameter line D used in the abduction angle α visualization. A typical acetabular shell 106 may have an anteversion angle v in a range of about 10° to about 30°, or about 10° to about 20°, or about 15° to about 25°. It will be appreciated that in practice, the alignment of the acetabular shell 106 within the reamed acetabulum 111 is a compound angle comprising both the abduction angle α and the anteversion angle v. Likewise, the alignment of the femoral stem 115 within the intramedullary bore 119 is a compound angle comprising both the abduction angle α and the anteversion angle v.

The anteversion angle v of the femoral stem 115 typically has the same range of values of the anteversion angle v of the acetabular shell 106 (i.e., a range of about 10° to about 30°, or about 10° to about 20°, or about 15° to about 25°) because having a femoral stem 115 that aligns with an acetabular shell 106 along a common angle of anteversion (or anteversion plane) is one of the alignment parameters of a properly aligned endoprosthetic hip implant 102. Placing the femoral stem 115 in the intramedullary canal of the proximal femur 105 such that the longitudinal axis of the femoral stem is co-linear with the anatomical axis of the femur 105 into which the femoral stem 115 is placed is another alignment parameter for a properly aligned femoral component 104 relative to a properly aligned acetabular component 103 to together define a properly aligned endoprosthetic hip implant 102. A third alignment parameter for the femoral stem 115 is the vertical position of the artificial femoral head 113 relative to the natural femoral head (see 126) of the operative hip prior to resection.

Figure 4:
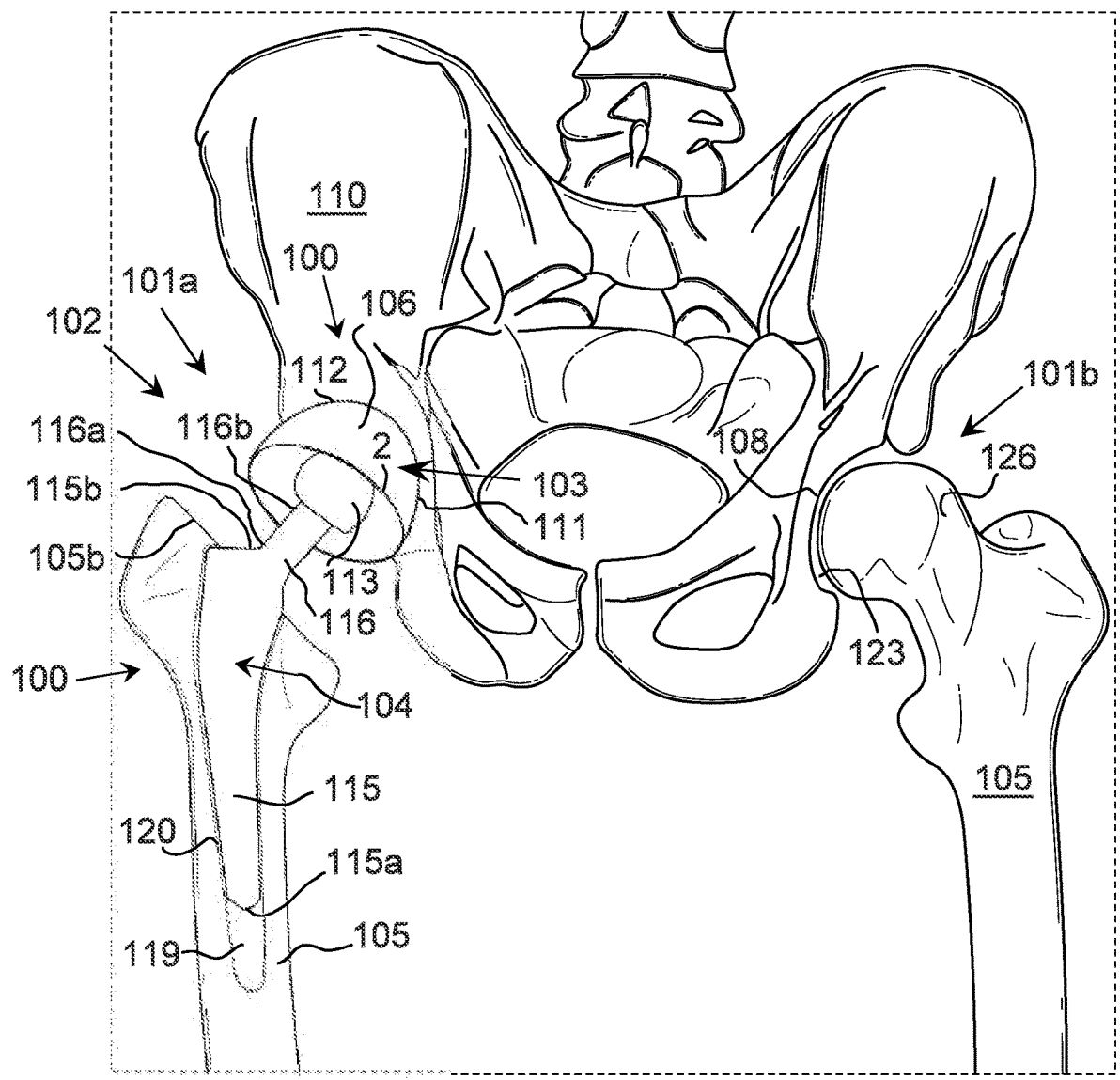
FIG. 4 depicts a misaligned acetabular cup and a mis-sized femoral stem.

FIG. 4 depicts a misaligned acetabular component 103 relative to the reamed acetabulum 111 and a femoral component 104 that is too short for the reamed femoral canal (also known as the intramedullary bore 119). As shown, the abduction angle α and the anteversion angle v are excessive. When the patient moves his or her hip during normal use, the neck 116 may contact the rim 2 of the acetabular shell 106. Collectively, the rim 2 and the neck 116 can become a fulcrum for a lever that can dislocate the artificial femoral head 113 from the acetabular component 103. Additionally, even if the femoral component 104 does not dislocate from the acetabular component 103, the force distribution of the femoral head 113 relative to the inner liner 107 may be overly concentrated in a relatively small area, thereby increasing wear and reducing the longevity of the implant 102.

FIG. 4 also depicts a femoral stem 115 that is improperly sized and aligned relative to the intramedullary bore 119. Improper sizing can occur when the femoral reaming (also known as a "broaching") tool does not create an intramedullary bore 119 that is large enough to remove cancellous bone that is peripheral to the inner cortical wall 120 of the femur 105. Over time, the femoral stem 115 will compress any intermediate cancellous bone between the side of the femoral stem 115 and the inner cortical wall 120, which will cause the femoral stem to subside in the intramedullary bore 119 and to become misaligned relative to the proximal femur 105. Variability in broach placement can also lead to a varus tilt in which the longitudinal axis of the femoral stem 115 is disposed at a varus angle relative to the anatomical (i.e., central, or longitudinal) axis of the distal femur 105. For example, it is common that the surgeon will contact the lateral cortical wall 120 of the intramedullary canal 119 above the desired location of the femoral stem 115. The surgeon may stop reaming upon contacting the lateral cortical wall 120 of the intramedullary canal 119 thinking that the patient has a narrow intramedullary canal 119 that will only accommodate a small femoral stem 115. In reality, the longitudinal axis of the femoral stem 115 is disposed at a varus angle relative to the anatomical axis of the distal femur 105. This subsidence and misalignment can ultimately change the length of one of the patient's legs relative to the other leg, which in turn alters the patient's gait. A halting gait changes the force distribution through the patient's body, which can further accelerate the wear of the endoprosthetic hip implant 102 as well as the wear of healthy cartilage 123 on the remaining natural hip joint 101b.

Subsidence and misalignment of the femoral component 104 relative to the distal femur 105 can be especially difficult to achieve and to check with traditional 2D radiographs. This is because the femoral component 104 is inserted into the proximal femur 105 through the six to eight inch main incision. The surgeon's view of insertion is limited by the minimally invasive nature of the procedure and the femoral component is no longer visible to the unassisted eye once it enters the intramedullary bore 119. Traditional 2D intraoperative radiographs (such a fluoroscopic images) do not show the third dimension, and therefore cannot provide an accurate real world depiction of the operative area 170 in 3D space.

Patient comfort and implant longevity are thought to depend in part on the placement and sizing of the artificial hip implant 102. In general, the more closely the placement of a properly sized implant replicates the natural kinematics of the pre-diseased joint, the longer the implant can be expected to last and the more comfort the patient can be expected to experience.

In recent years, it has become possible to use 2D images, such as X-ray radiographs, to create 3D models of an operative area. These models can be used preoperatively to plan surgeries much closer to the date of the actual surgery. These models can also be used intraoperatively (e.g., when projected on a display or across a surgeon's field of view).

However, X-ray radiographs have typically not been used as inputs for 3D models previously because of concerns about image resolution and accuracy. X-ray radiographs are 2D representations of 3D space. As such, a 2D X-ray radiograph necessarily distorts the image subject relative to the actual object that exists in three dimensions. Furthermore, the object through which the X-ray passes can deflect the path of the X-ray as it travels from the X-ray source 21 (typically the anode of the X-ray machine; see FIG. 12) to the X-ray detector 33 (which may include by non-limiting example, X-ray image intensifiers, phosphorus materials, flat panel detectors "FPD" (including indirect conversion FPDs and direct conversion FPDs), or any number of digital or analog X-ray sensors or X-ray film; see FIG. 12). Defects in the X-ray machine (see 1800, FIG. 12) itself or in its calibration can also undermine the usefulness of X-ray photogrammetry and 3D model reconstruction. Additionally, emitted X-ray photons have different energies. As the X-rays interact with the matter placed between the X-ray source 21 and the detector 33, noise and artifacts can be produced in part because of Compton and Rayleigh scattering, the photoelectric effect, extrinsic variables in the environment or intrinsic variables in the X-ray generation unit, X-ray detector, and/or processing units or displays.

Moreover, in a single 2D image, the 3D data of the actual subject is lost. As such, there is no data that a computational machine 1600 (e.g., a computer) can use from a single 2D image to reconstruct a 3D model of the actual 3D object. For this reason, CT scans, MRIs, and other imaging technologies that preserve third dimensional data were often preferred inputs for reconstructing models of one or more subject orthopedic elements (i.e., reconstructing a 3D model from actual 3D data generally resulted in more accurate, higher resolution models). However, certain exemplary embodiments of the present disclosure that are discussed below overcome these issues by using deep learning networks to improve the accuracy of reconstructed 3D models generated from X-ray input images.

There are a variety of methods to generate a 3D model from 2D preoperative or intraoperative images. By way of example, one such method may comprise receiving a set of 2D radiographic images of an operative area 170 of a patient with a radiographic imaging system, computing a first 3D model using epipolar geometry principles with a coordinate system of the radiographic imaging system and projective geometry data from the respective 2D images (see FIGS. 8 and 9A, 9B and 9C). Such an exemplary method may further comprise projecting the first 3D model on the 2D radiographic images and then adjusting the initial 3D model by registering the first and second radiographic images 30, 50 on the first 3D model with an image-to-image registration technique. Once the image-to-image registration technique has been applied, a revised 3D model may be generated. This process can repeat until the desired clarity in achieved.

By way of another example, a deep learning network (also known as a "deep neural network" ("DNN"), such as a convolutional neural network ("CNN"), recurrent neural network ("RNN"), modular neural network, or sequence to sequence model, can be used to generate a 3D model of the subject orthopedic element (i.e., a modeled orthopedic element 100b) from a set of at least two 2D images of an operative area 170 of a patient. The 2D input images 30, 50, etc. are desirably tissue-penetrating images, such as radiographic images (e.g., X-ray or fluoroscopy images). In such a method, the deep learning network can generate a model from the projective geometry data (i.e., spatial data 43 or volume data 75) from the respective 2D images. The deep learning network can have the advantage of being able to generate a mask of the different subject orthopedic elements 100 (e.g., bones, soft tissues, etc.) in the operative area 170 as well as being able to calculate a volume (see 61, FIG. 7) of one or more imaged orthopedic elements 100. In exemplary embodiments, the dimensions of the identified orthopedic element 100 or of the component of an endoprosthetic implant assembly 102 can be mapped to spatial data 43 (FIG. 8) that is derived from the input images 30, 50 (FIG. 8) to ascertain the position of the identified orthopedic element 100 or the component of the endoprosthetic implant assembly in 3D space. In this manner, the positions of the identified orthopedic element 100 and of the component of the endoprosthetic implant (e.g., an acetabular component 104 or a femoral component 103) can be ascertained relative to each other. If this information is displayed to the surgeon and is updated in real time or near real time based upon the surgeon's repositioning of the implant component relative to the identified orthopedic element, the surgeon can use exemplary embodiments in accordance with this disclosure to accurately align the implant component relative to the identified orthopedic element in three dimensions, while bypassing the limited field of view offered by the main incision.

It is contemplated that once the system is calibrated as discussed below, new tissue-penetrating images (i.e., less than the number of input images needed to calibrate the system) can be taken intraoperatively to update the reconstructed model of the operative area (e.g., to refresh the position of the identified component of the endoprosthetic implant related to another component of an endoprosthetic implant or relative to an identified orthopedic element). In other exemplary embodiments, the same number of new tissue-penetrating images as the number of input images chosen to calibrate the system can be used to refresh the position of the component of the endoprosthetic implant relative to another component of an endoprosthetic implant, or relative to and identified orthopedic element in the system.

Figure 5:
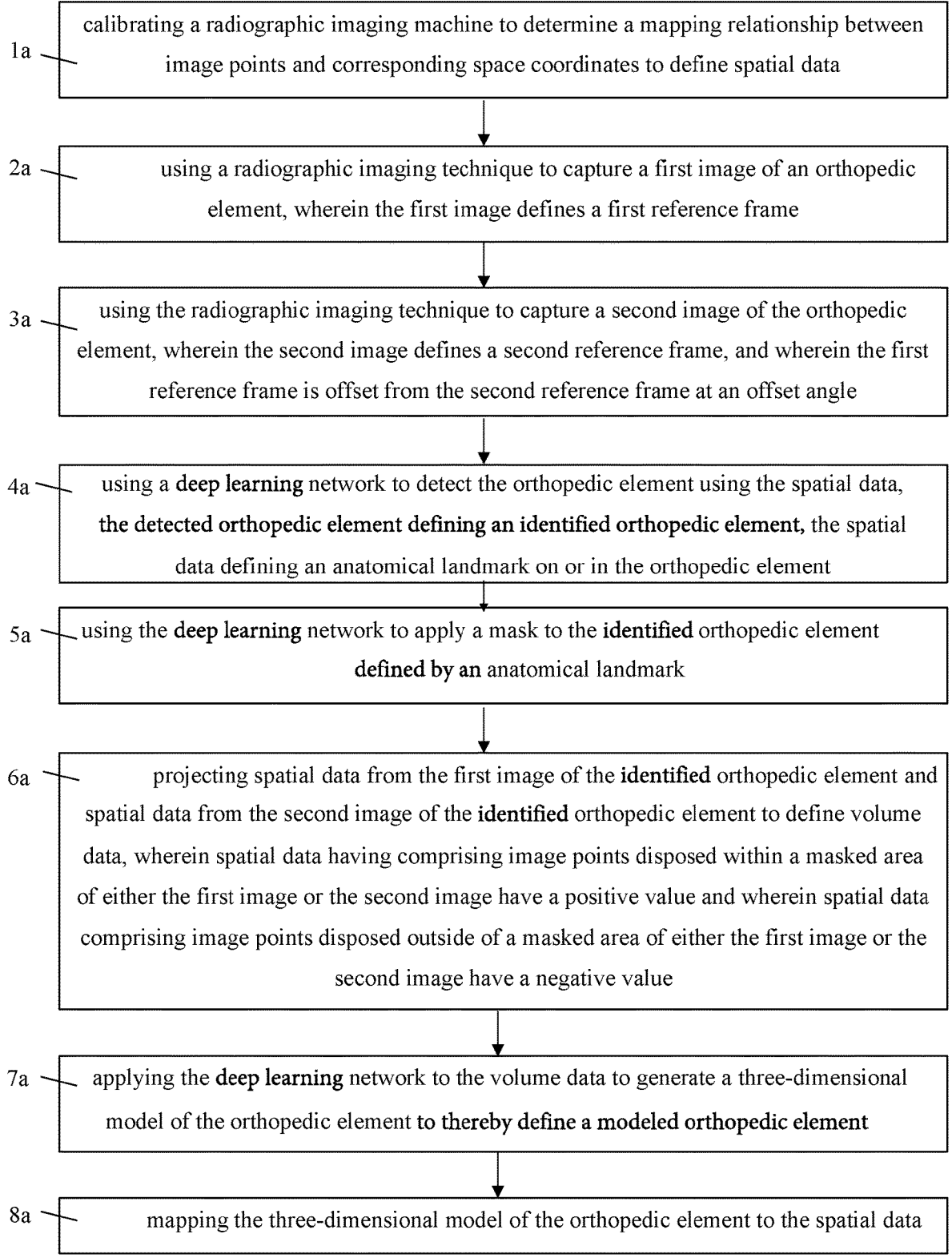
FIG. 5 is a flow chart illustrating steps of an exemplary method.

FIG. 5 is a flow chart outlining the steps of an exemplary method for ascertaining a position of an orthopedic element in space. The method comprises: step 1a calibrating a tissue-penetrating machine, such as a radiographic imaging machine 1800 to determine a mapping relationship between image points (e.g., $X_L$, $X_R$; FIG. 8) and corresponding space coordinates (e.g., x and y coordinates; FIG. 8) to define spatial data 43, step 2a capturing a first image 30 (FIG. 8) of an orthopedic element 100 using a radiographic imaging technique, wherein the first image 30 defines a first reference frame 30a, step 3a capturing a second image 50 (FIG. 8) of the orthopedic element 100 using the radiographic imaging technique, wherein the second image 50 defines a second reference frame 50a, and wherein the first reference frame 30a is offset from the second reference frame 50a at an offset angle θ, step 4a using a deep learning network to detect the orthopedic element using the spatial data 43, the spatial data 43 defining anatomical landmarks on or in the orthopedic element 100, the detected orthopedic element defining an identified orthopedic element 100a, step 5a using the deep learning network to apply a mask to the identified orthopedic element 100a defined by an anatomical landmark, step 6a projecting the spatial data 43 from the first image 30 of the identified orthopedic element 100a and the spatial data 43 from the second image 50 of the identified orthopedic element 100a to define volume data 75 (FIG. 7), wherein the spatial data 43 comprising image points (e.g., $X_L$, $X_R$) disposed within a masked area of either the first image 30 or the second image 50 have a first value and wherein the spatial data 43 comprising image points (e.g., $X_L$, $X_R$) disposed outside of a masked area of either the first image 30 or the second image 50 have a second value, wherein the first value is different from the second value, step 7a applying the deep learning network to the volume data 75 to generate a reconstructed 3D model of the orthopedic element, to define a modeled orthopedic element 100b; and step 8a mapping the 3D modeled orthopedic element 100b to the spatial data 43. In other exemplary embodiments, step 4a can comprise detecting the spatial data 43 defining anatomical landmarks on or in the orthopedic element 100 using a deep learning network.

Figure 6:
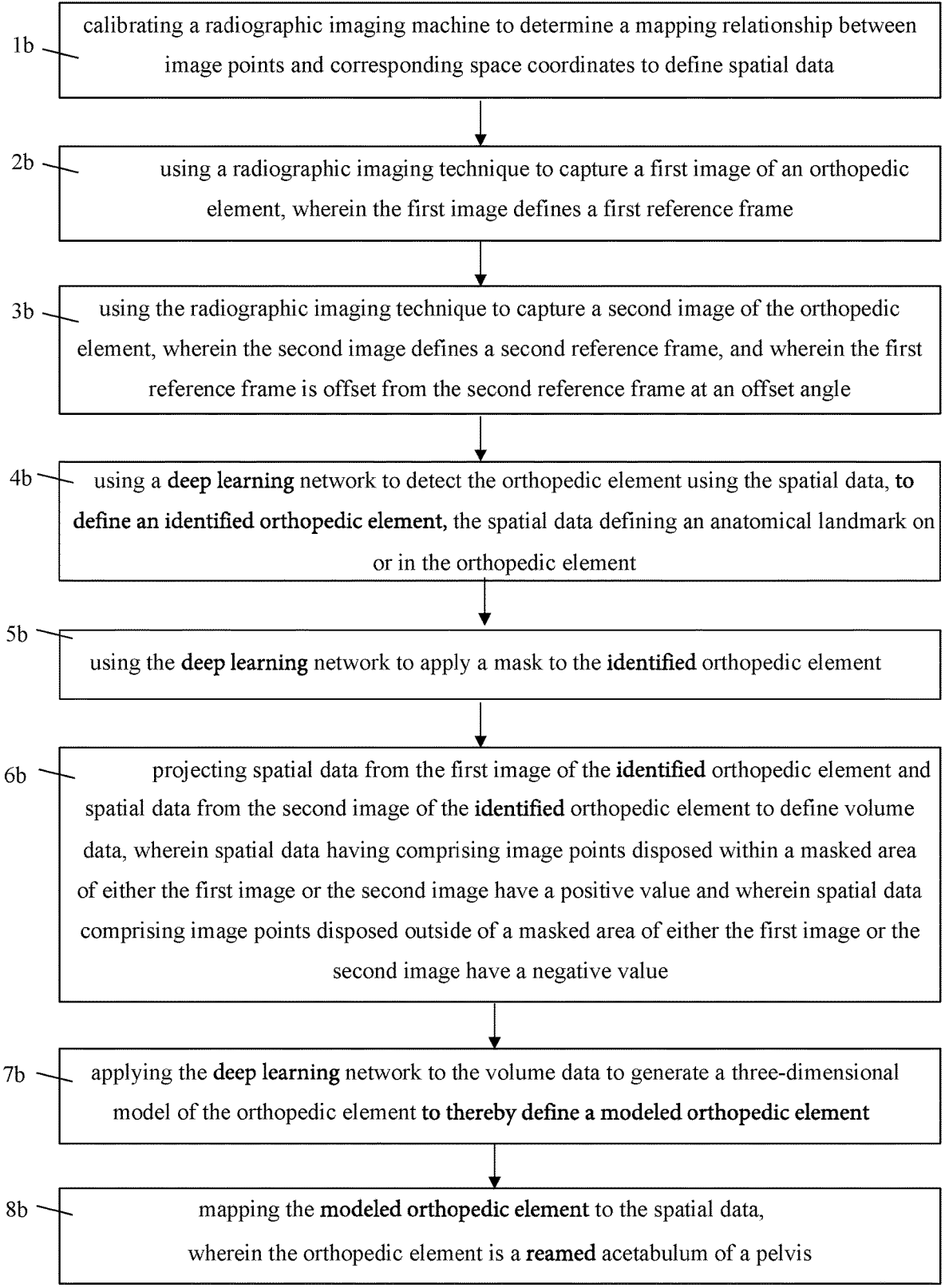
FIG. 6 is a flow chart illustrating steps of a further exemplary method.

FIG. 6 is a flow chart outlining the steps of another exemplary method for ascertaining a position of an orthopedic element in space. The method comprises: step 1b calibrating a tissue-penetrating imaging machine, such as a radiographic imaging machine to determine a mapping relationship between image points (e.g., $X_L$, $X_R$) and corresponding space coordinates (e.g., x and y coordinates) to define spatial data 43, step 2b capturing a first image 30 of an orthopedic element 100 using a radiographic imaging technique, wherein the first image 30 defines a first reference frame 30a, step 3b capturing a second image 50 of the orthopedic element 100 using the radiographic imaging technique, wherein the second image 50 defines a second reference frame 50a, and wherein the first reference frame 30a is offset from the second reference frame 50a at an offset angle θ, step 4b using a deep learning network to detect the orthopedic element 100 using the spatial data 43 to define an identified orthopedic element 100a, the spatial data 43 defining anatomical landmarks on or in the orthopedic element 100, step 5b using the deep learning network to apply a mask to the identified orthopedic element 100a defined by an anatomical landmark, step 6b projecting the spatial data 43 from the first image 30 of the identified orthopedic element 100a and the spatial data 43 from the second image 50 of the identified orthopedic element 100a to define volume data 75, wherein the spatial data 43 comprising image points (e.g., $X_L$, $X_R$) disposed within a masked area of either the first image 30 or the second image 50 have a first value and wherein the spatial data 43 comprising image points (e.g., $X_L$, $X_R$) disposed outside of a masked area of the either the first image 30 or the second image 50 have a second value, wherein the first value is different from the second value, step 7b applying the deep learning network to the volume data 75 to generate a reconstructed 3D model of the orthopedic element to define a modeled orthopedic element 100b; and step 8b mapping the modeled orthopedic element 100b to the spatial data 43, wherein the orthopedic element is a reamed acetabulum 111 of a pelvis 110. In other exemplary embodiments, step 4b can comprise detecting the spatial data 43 defining anatomical landmarks on or in the identified orthopedic element 100a using a deep learning network.

It will be appreciated that in certain exemplary embodiments, the deep learning network can be the same deep learning network that has been separately trained to perform the discrete tasks (e.g., identification of the orthopedic element 100 to define an identified orthopedic element 100a, applying a mask to the identified orthopedic element 100a, modeling the identified orthopedic element 100a to define a modeled orthopedic element 100b, etc.). In other exemplary embodiments, a different deep learning network can be used to perform one or more of the discrete tasks.

It is contemplated that exemplary methods and systems in accordance with this disclosure may be used in connection with a total hip arthroplasty ("THA"). In such exemplary embodiments, the orthopedic element 100 can be a femur 105, femoral head 126, pelvis 110, acetabular cavity of the pelvis (e.g., a natural acetabulum 108 or a reamed acetabulum 111), and other boney anatomical landmark present in or near the operative area 170. However, it will be appreciated that nothing in this disclosure limits the application of the exemplary systems and methods to use in a THA procedure. It is contemplated that exemplary systems and methods can be useful in any surgical procedure in which the presence of a significant amount of tissue obscures the view of the orthopedic element 100 or of the operative area 170 generally. Surgeries involving the shoulder, knee, or spine can be prime examples. Pediatric cardiothoracic procedures can be another example. Systems and methods in accordance with the present disclosure can further be useful with wrist and ankle procedures even though the surgeon's visual field is generally less obscured by surrounding tissue than in shoulder, hip, and spinal procedures.

The above examples are provided for illustrative purposes and are in no way intended to limit the scope of this disclosure. All methods for generating a 3D model from 2D radiographic images of the same subject taken from at least two transverse positions are considered to be within the scope of this disclosure.

Figure 7:
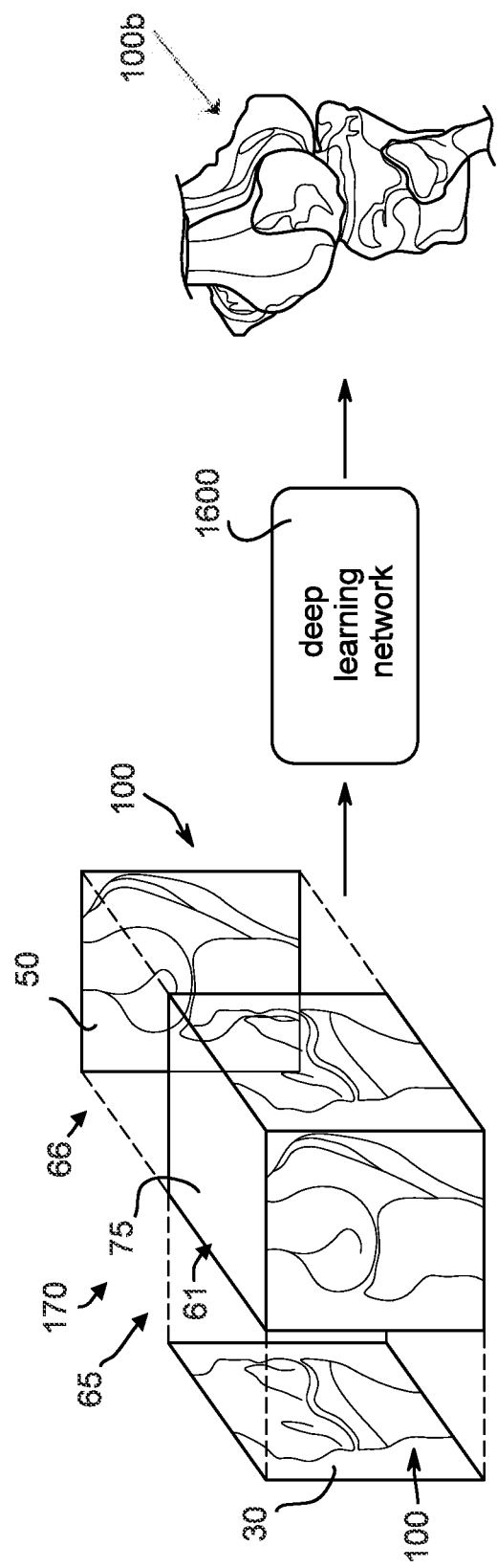
FIG. 7 is a schematic depiction of a system that uses a deep learning network to identify features (e.g., anatomical landmarks) of a subject orthopedic element to generate a 3D model of the subject orthopedic element.
Figure 8:
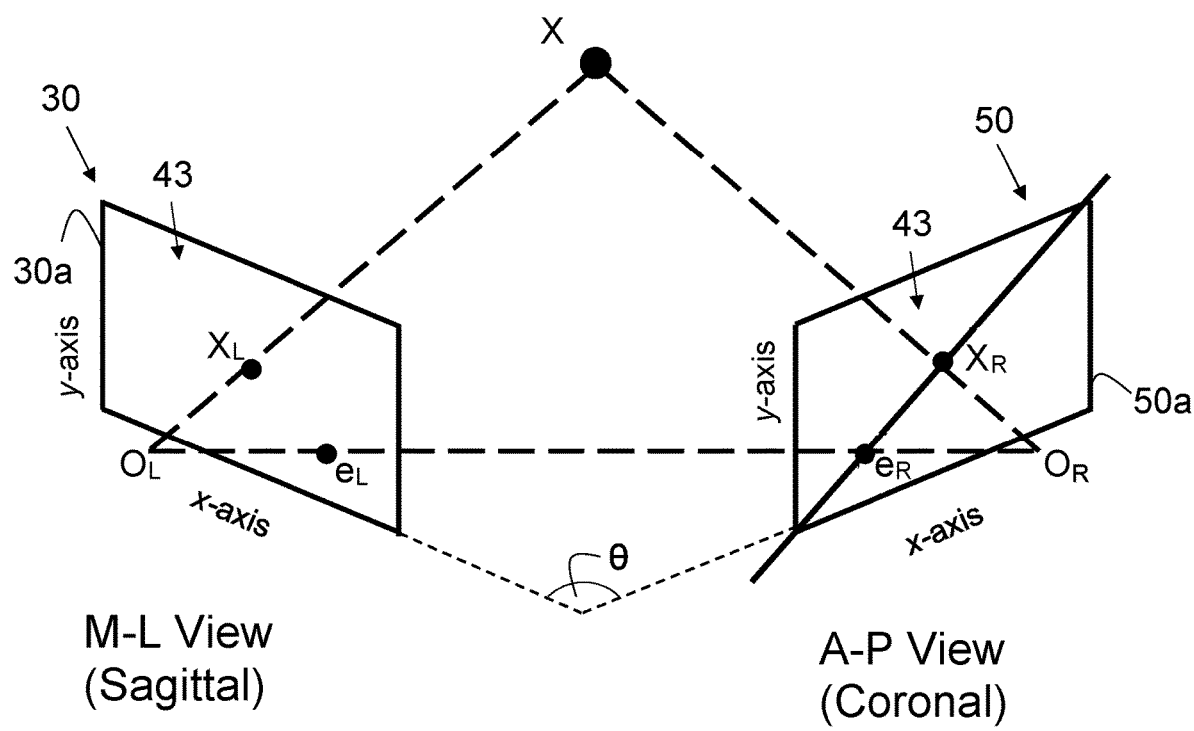
FIG. 8 is a schematic depiction of a pinhole camera model used to convey how principles of epipolar geometry can be used to ascertain the position of a point in 3D space from two 2D images taken from different reference frames from calibrated image detectors.

FIGS. 7 and 8 illustrate how the first input image 30 and the second input image 50 can be combined to create a volume 61 comprising volume data 75 (FIG. 7). In FIG. 7, the imaged operative area 170 is of a knee joint. FIG. 7 provides an example of how a deep learning network can take volume data 75 from two calibrated input images 30, 50 that are offset from one another by an offset angle θ, can generate one or more modeled orthopedic elements 100b from the volume data 75. In FIG. 7, the operative area 170 is that of a knee joint.

FIG. 8 illustrates basic principles of epipolar geometry than can be used to convert spatial data 43 from the respective input images 30, 50 into volume data 75. It will be appreciated that the spatial data 43 is defined by a collection of image points (e.g., $X_L$, $X_R$) mapped to corresponding space coordinates (e.g., x and y coordinates) for a given input image 30, 50.

Figure 12:
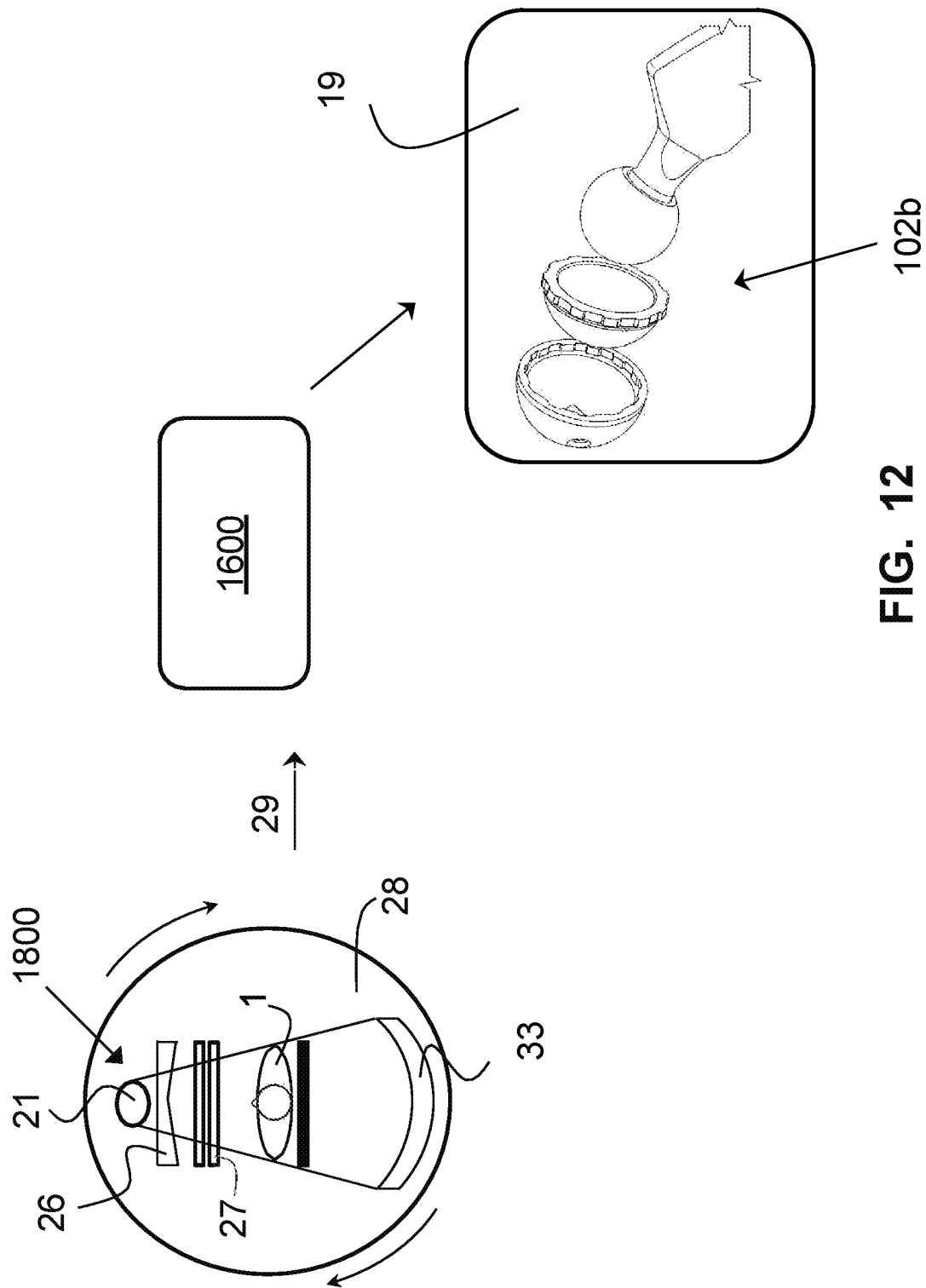
FIG. 12 is a schematic representation of an exemplary system.

FIG. 8 is a simplified schematic representation of a perspective projection described by the pinhole camera model. FIG. 8 conveys basic concepts related to computer stereo vison, but it is by no means the only method by which 3D models can be reconstructed from 2D stereo images. In this simplified model, rays emanate from the optical center (i.e., the point within a lens at which the rays of electromagnetic radiation (e.g., visible light, X-rays, etc.) from the subject object are assumed to cross within the imaging machine's sensor or detector array 33 (FIG. 12). The optical centers are represented by points $O_L$, $O_R$ in FIG. 8. In reality, the image plane (see 30a, 50a) is usually behind the optical center (e.g., $O_L$, $O_R$) and the actual optical center is projected onto the detector array 33 as a point, but virtual image planes (see 30a, 50a) are presented here for illustrating the principles more simply.

The first input image 30 is taken from a first reference frame 30a, while the second input image 50 is taken from a second reference frame 50a that is different from the first reference frame 30a. Each image comprises a matrix of pixel values. The first and second reference frames 30a, 50a are desirably offset from one another by an offset angle θ. The offset angle θ can represent the angle between the x-axis of the first reference frame 30a relative to the x-axis of the second reference frame 50a. Stated differently, the angle between the orientation of the orthopedic element in the first image and the orthopedic element in the second image can be known as the "offset angle."

Point $e_L$ is the location of the second input image's optical center $O_R$ on the first input image 30. Point $e_R$ is the location of the first input image's optical center $O_L$ on the second input image 50. Points $e_L$ and $e_R$ are known as "epipoles" or epipolar points and lie on line $O_L$-$O_R$. The points X, $O_L$, $O_R$ define an epipolar plane.

Because the actual optical center is the assumed point at which incoming rays of electromagnetic radiation from the subject object cross within the detector lens, in this model, the rays of electromagnetic radiation can actually be imagined to emanate from the optical centers $O_L$, $O_R$ for the purpose of visualizing how the position of a 3D point X in 3D space can be ascertained from two or more input images 30, 50 captured from a detector 33 of known relative position. If each point (e.g., $X_L$) of the first input image 30 corresponds to a line in 3D space, then if a corresponding point (e.g., $X_R$) can be found in the second input image, then these corresponding points (e.g., $X_L$, $X_R$) must be the projection of a common 3D point X. Therefore, the lines generated by the corresponding image points (e.g., $X_L$, $X_R$) must intersect at 3D point X. In general, if the value of X is calculated for every corresponding image points (e.g., $X_L$, $X_R$) in two or more input images 30, 50, a 3D volume 61 comprising volume data 75 can be reproduced from the two or more input images 30, 50. The value of any given 3D point X can be triangulated in a variety of ways. A non-limiting list of example calculation methods include the mid-point method, the direct linear transformation method, the essential matrix method, the line-line intersection method, and the bundle adjustment method. Furthermore, in certain exemplary embodiments, a deep learning network can be trained on a set of input images to establish a model for determining the position of a given point in 3D space based upon two or more input images of the same subject, wherein the first input image 30 is offset from the second input image 50 at an offset angle θ. It will be further appreciated that combinations of any of the above methods are within the scope of this disclosure.

It will be appreciated that "image points" (e.g., $X_L$, $X_R$) described herein may refer to a point in space, a pixel, a portion of a pixel, or a collection of adjacent pixels. It will also be appreciated that 3D point X as used herein can represent a point in 3D space. In certain exemplary applications, 3D point X may be expressed as a voxel, a portion of a voxel, or a collection of adjacent voxels.

Figure 9A:
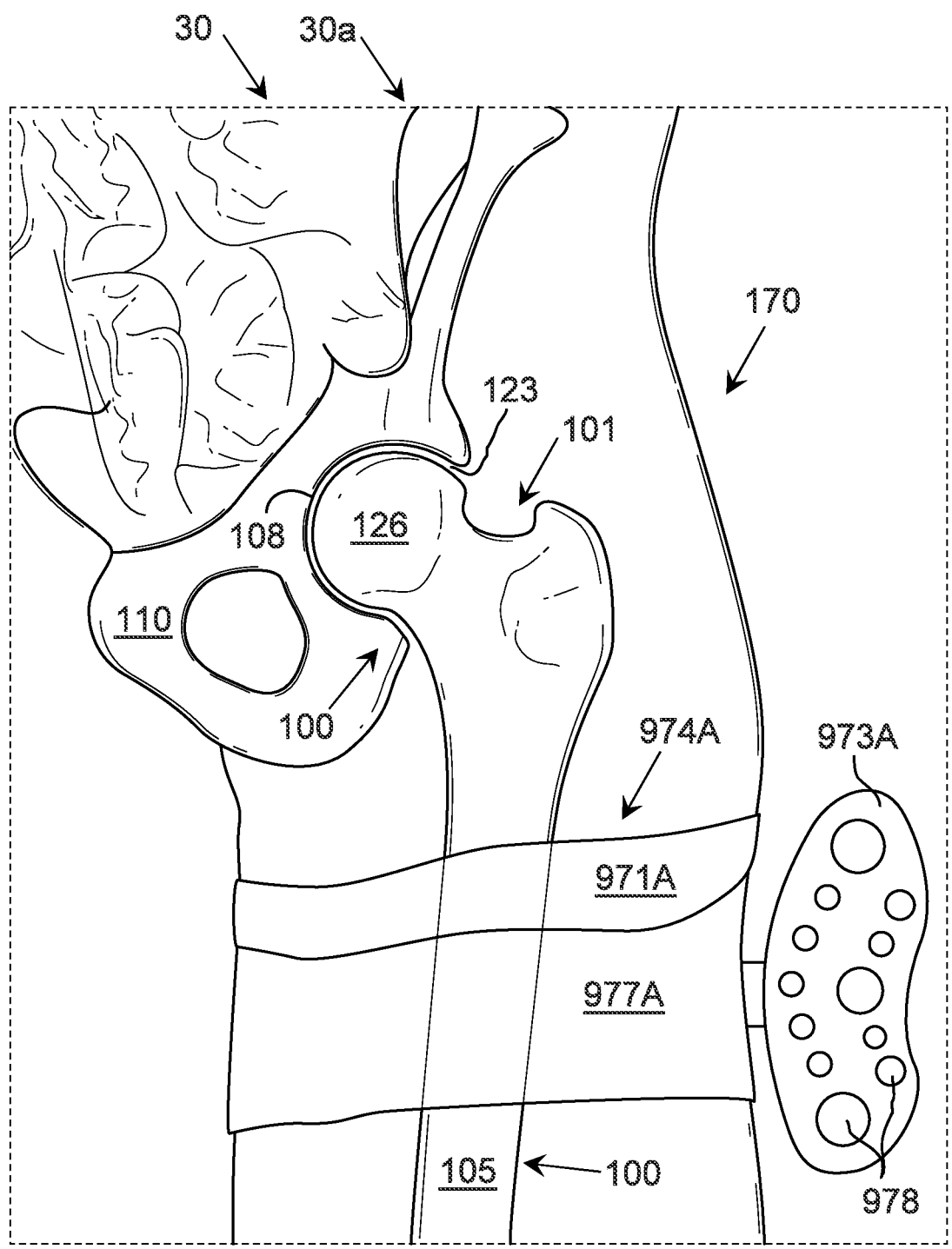
FIG. 9A is an image of the subject orthopedic elements taken from the anterior-posterior ("A-P") position that shows an exemplary calibration jig.
Figure 9B:
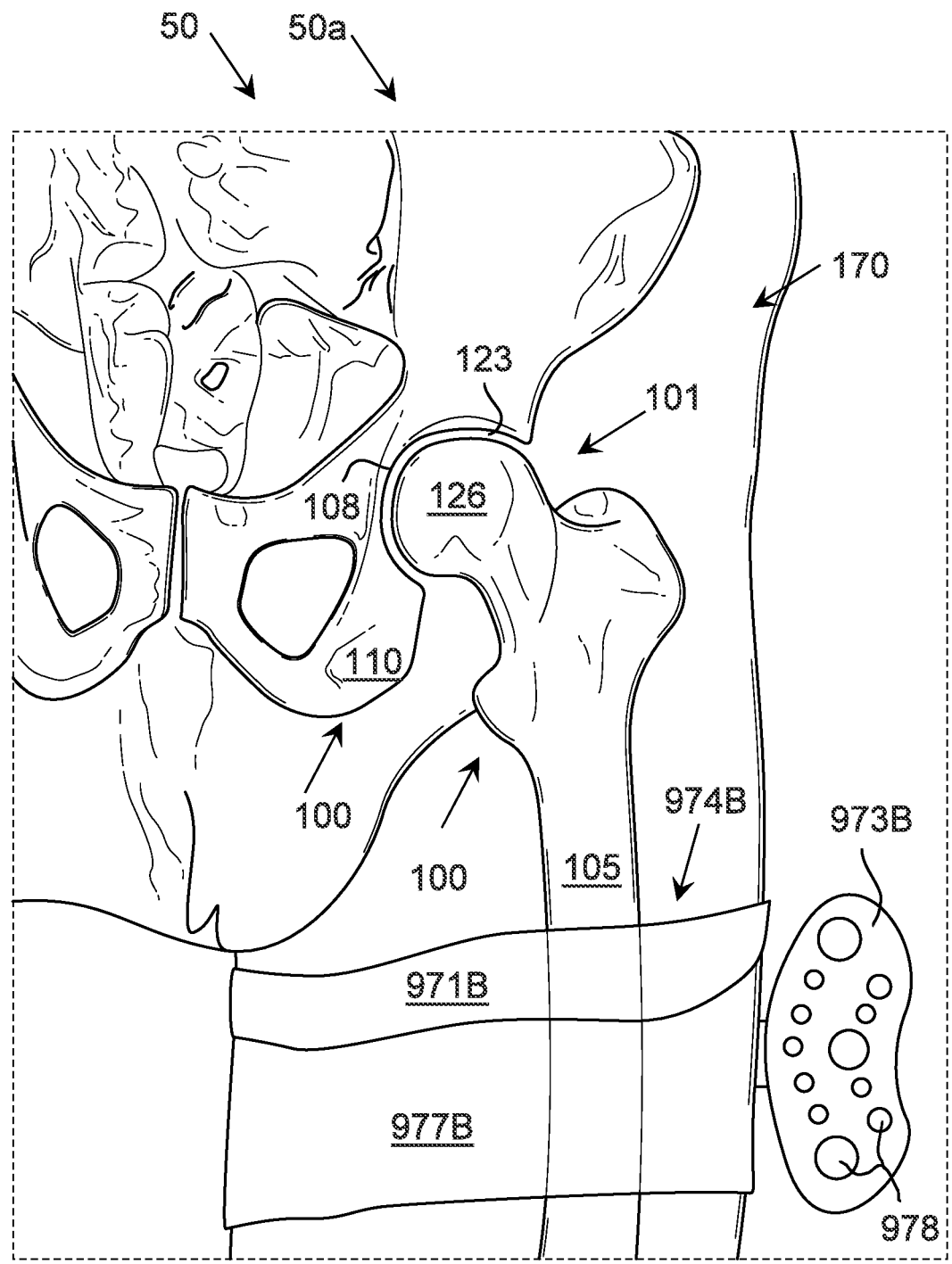
FIG. 9B is an image of the subject orthopedic elements of FIG. 9A taken at about 45° clockwise from reference frame of FIG. 9A with the calibration jig.
Figure 9C:
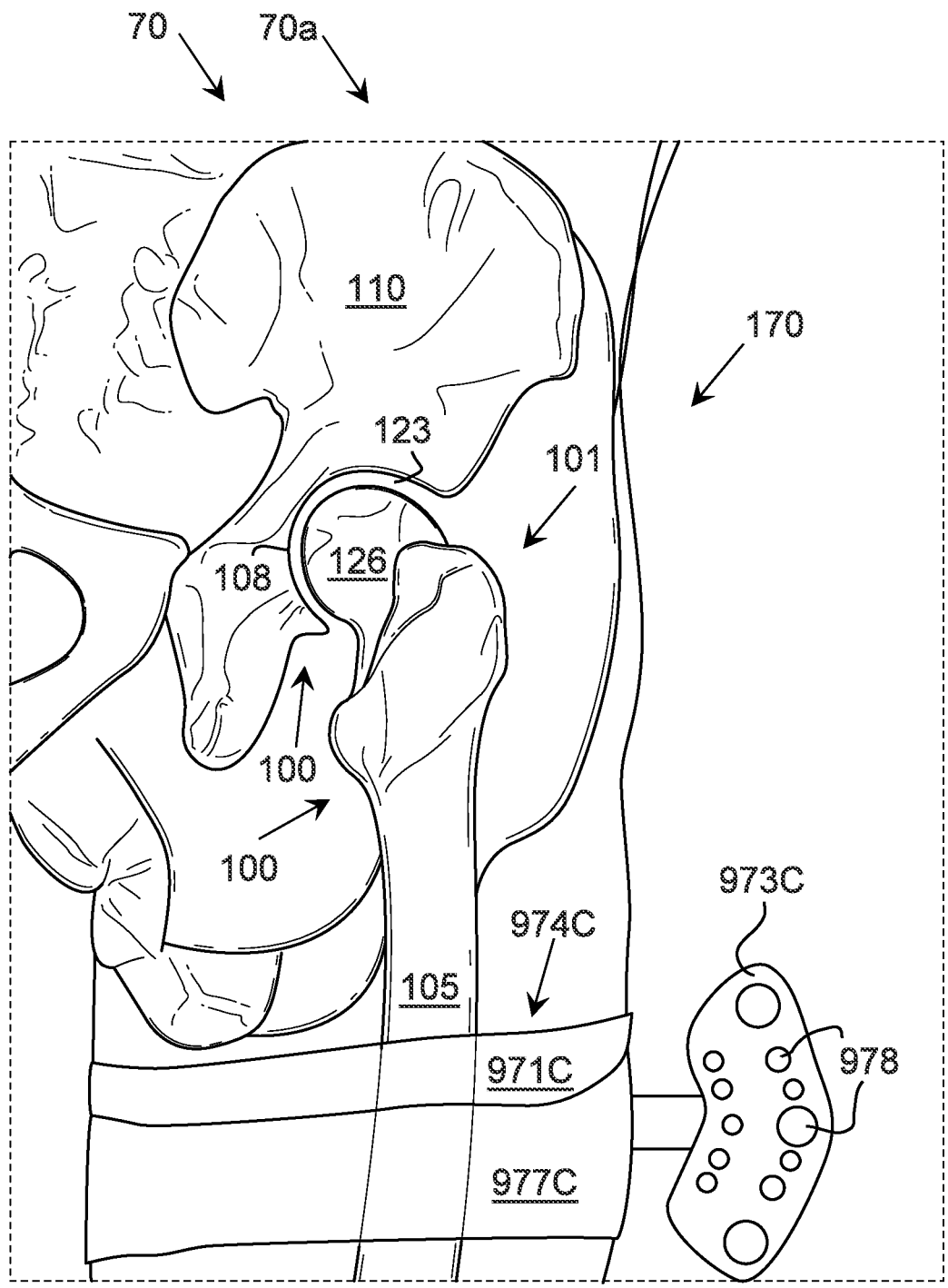
FIG. 9C is an image of the subject orthopedic elements of FIG. 9A taken at about 45° counterclockwise from reference frame of FIG. 9A with the calibration jig.

However, before principles of epipolar geometry can be applied, the position of each image detector 33 relative to the other image detector(s) 33 should be determined (or the position of a sole image detector 33 must be determined at the point in time in which the first image 30 was taken and the adjusted position of the sole image detector 33 should be known at the point in time in which the second image 50 was taken). It can also be desirable to determine the focal length and the optical center of the imaging machine 1800. To ascertain this practically, the image detector 33 (or image detectors) is/are first calibrated. FIGS. 9A, 9B, and 9C depict calibration jigs 973A, 973B, 973C relative to subject orthopedic elements 100. In these figures, the example orthopedic elements 100 include are the proximal aspect of the femur 105 and the natural acetabulum 108 of the pelvis 110 that comprises a hip joint 101.

Although at least two input images 30, 50 are technically required for calibrating the exemplary systems described herein, at least three input images 30, 50, 70 can be desirable when the input images are radiographic input images and wherein the target operative area 170 involves a contralateral joint that cannot be easily isolated from radiographic imaging. For example, the pelvis 110 comprises contralateral acetabula 108. A direct medial-lateral radiograph of the pelvis 110 would show both the acetabulum that is proximal to the detector 33 and the acetabulum that is distal to the detector 33. However, because of the positioning of the pelvis 110 relative to the detector 33 and because a single 2D radiograph lacks 3D data, the relative acetabula will appear superimposed upon one another and it would be difficult for a person or a computational machine 1600 to distinguish which is the proximal and which is the distal acetabulum.

To address this issue, at least three input images 30, 50, 70 can be used. In one exemplary embodiment, the first input image 30 can be a radiograph that captures an anterior-posterior perspective of the operative area 170 (i.e., an example of a first reference frame 30a). For the second input image 50, the patient or the detector 33 can be rotated clockwise (which can be designated by a positive degree) or counterclockwise (which can be designated by a negative degree) relative to the patient's orientation for the first input image 30. For example, for the second input image 50, the patient may be rotated plus or minus 45° from the patient's orientation in the first input image 30. Likewise, the patient may be rotated clockwise or counterclockwise relative to the patient's orientation for the first input image 30. For example, for the third input image 70, the patient may be rotated plus or minus 45° relative to the patient's orientation in the first input image 30. It will be appreciated that if the second input image 50 has a positive offset angle (e.g., +45°) relative to the orientation of the first input image 30, the third input angle 70 desirably has a negative offset angle (e.g., −45°) relative to the orientation of the first input image 30 and vice versa.

In exemplary embodiments, the principles or epipolar geometry can be applied to at least three input images 30, 50, 70 taken from at least three different reference frames 30a, 50a, 70a to calibrate exemplary systems.

FIG. 9A is an anterior-posterior view of the example orthopedic elements 100 (e.g., a proximal femur 105, a natural acetabulum 108, a pelvis 110, articular cartilage, other soft tissue, etc.) in an example operative area 170. That is, FIG. 9A represents a first image 30 taken from a first reference frame 30a (e.g., a first transverse position). A first calibration jig 973A is attached to a first holding assembly 974A. The first holding assembly 974A may comprise a first padded support 971A engaged to a first strap 977A. The first padded support 971A is attached externally to the patient's thigh via the first strap 977A. The first holding assembly 974A supports the first calibration jig 973A that is oriented desirably parallel to the first reference frame 30a (i.e., orthogonal to the detector 33). The calibration jig 973A is desirably positioned sufficiently far away from the desired subject orthopedic elements 100 such that the calibration jig 973A do not overlap any subject orthopedic element 100. Overlapping my obscure desirable image data.

FIG. 9B is a view of the example orthopedic elements 100 (e.g., a proximal femur 105, a natural acetabulum 108, a pelvis 110, articular cartilage, other soft tissue, etc.) of the example operative area 170 of FIG. 9A that is positively offset from the first reference frame 30a by 45°. That is, FIG. 9B represents a second input image 50 taken from a second reference frame 50a (e.g., a second transverse position). A second calibration jig 973B is attached to the second holding assembly 974B. The second holding assembly 974B may comprise a second padded support 971B engaged to a second strap 977B. The second padded support 971B is attached externally to the patient's thigh via the second strap 977B. The second holding assembly 974B supports the second calibration jig 973B that is oriented desirably parallel to the second reference frame 50a (i.e., orthogonal to the detector 33). The calibration jig 973B is desirably positioned sufficiently far away from the subject orthopedic elements 100 such that the calibration jig 973B does not overlap any subject orthopedic element 100.

FIG. 9C is a view of the example orthopedic elements 100 (e.g., a proximal femur 105, a natural acetabulum 108, a pelvis 110, articular cartilage, other soft tissue, etc.) of the example operative area 170 of FIG. 9A that is negatively offset from the first reference frame 30a by 45°. That is, FIG. 9C represents a third input image 70 taken from a third reference frame 70a (e.g., a third transverse position). A third calibration jig 973C is attached to the third holding assembly 974C. The third holding assembly 974C may comprise a third padded support 971C engaged to a third strap 977C. The third padded support 971C is attached externally to the patient's thigh via the third strap 977C. The third holding assembly 974C supports the third calibration jig 973C that is oriented desirably parallel to the third reference frame 70a (i.e., orthogonal to the detector 33). The calibration jig 973C is desirably positioned sufficiently far away from the subject orthopedic elements 100 such that the calibration jig 973C does not overlap any subject orthopedic element 100.

If the system is calibrated preoperatively, the patient may be posited in the standing position (i.e., the leg is in extension) because the hip joint is stable in this orientation (see FIG. 12). If the system is calibrated intraoperatively, the patient may be lying supine on the operating table. Preferably, the patient's distance relative to the imaging machine should not be altered during the acquisition of the input images 30, 50, 70. The first, second, and third input images 30, 50, 70 need not capture the entire leg, rather the image can focus on the joint that will be the subject of the operative area 170.

It will be appreciated that depending upon the subject orthopedic elements 100 to be imaged and modeled, only a single calibration jig 973 may be used. Likewise, if a particularly long collection of orthopedic elements 100 are to be imaged and modeled, more than one calibration jigs 973 may be used.

Each calibration jig 973A, 973B, 973C is desirably of a known size. Each calibration jig 973A, 973B, 973C desirably has at least four or more calibration points 978 distributed throughout. The calibration points 978 are distributed in a known pattern in which the distance from one point 978 relative to the others is known. The distance from the calibration jig 973 from an orthopedic element 100 can also desirably be known. For calibration of an X-ray photogrammetry system, the calibration points 978 may desirably be defined by metal structures on the calibration jig 973. Metal typically absorbs most X-ray beams that contact the metal. As such, metal typically appears very brightly relative to material that absorbs less of the X-rays (such as air cavities or adipose tissue). Common example structures that define calibration points include, but are not limited to: reseau crosses, circles, triangles, pyramids, and spheres.

These calibration points 978 can exist on a 2D surface of the calibration jig 973, or 3D calibration points 978 can be captured as 2D projections from a given image reference frame. In either situation, the 3D coordinate (commonly designated the z coordinate) can be set to equal zero for all calibration points 978 captured in the image. The distance between each calibration point 978 is known. These known distances can be expressed as x, y coordinates on the image sensor/detector 33. To map a point in 3D space to a 2D coordinate pixel on a sensor 33, the dot product of the detector's calibration matrix, the extrinsic matrix and the homologous coordinate vector of the real 3D point can be used. This permits the real world coordinates of a point in 3D space to be mapped relative to calibration jig 973. Stated differently, this generally permits the x, y coordinates of the real point in 3D space to be transformed accurately to the 2D coordinate plane of the image detector's sensor 33 to define spatial data 43 (see FIG. 8).

The above calibration method is provided as an example. It will be appreciated that all methods suitable for calibrating an X-ray photogrammetry system are considered to be within the scope of this disclosure. A non-limiting list of other X-ray photogrammetry system calibration methods include the use of a reseau plate, the Zhang method, the bundle adjustment method, direct linear transformation methods, maximum likelihood estimation, a k-nearest neighbor regression approach ("KNN"), a convolutional neural network ("CNN") based approach, other deep learning methods, or combinations thereof.

FIG. 7 illustrates the principle of how two calibrated input images 30, 50, when oriented along the known offset angle θ, can be back projected into a 3D volume 61 comprising two channels 65, and 66. The first channel 65 contains all the image points (e.g., $X_L$ etc.) of the first input image 30 and the second channel 66 contains all the image points (e.g., $X_R$ etc.) of the second input image 50. That is, each image point (e.g., pixel) is replicated over its associated back-projected 3D ray. Next, epipolar geometry can be used to generate a volume 61 of the imaged operative area 170 comprising volume data 75 from these back projected 2D input images 30, 50. If a third input image 70 is used, a third channel containing all of the image points of the third input image 70 can be present.

Referring to FIG. 7, the first input image 30 and the second input image 50 desirably have known image dimensions. The dimensions may be pixels. For example, the first image 30 may have dimensions of 164×164 pixels. The second image 50 may have dimensions of 164×164 pixels. The dimensions of the input images 30, 50 used in a particular computation desirably have consistent dimensions. Consistent dimensions may be desirable for later defining a cubic working area of regular volume 61 (e.g., a 164×164×164 cube). In embodiments, the offset angle θ is desirably 45° between each adjacent input image. However, other offset angles θ may be used in other exemplary embodiments. For example, in FIG. 7, the offset angle θ is 90°.

In the depicted example, each of the 164×164 pixel input images 30, 50 are replicated 164 times over the length of the adjacent input image to create a volume 61 having dimensions of 164×164×164 pixels. That is, the first image 30 is copied and stacked behind itself at one copy per pixel for 164 pixels while the second image 50 is copied and stacked behind itself such that stacked images overlap to thereby create the volume 61. In this manner, the volume 61 can be said to comprise two channels 65, 66, wherein the first channel 65 comprises the first image 30 replicated n times over the length of the second image 50 (i.e., the x-axis of the second image 50) and the second channel 66 comprises the second image 50 replicated m times over the length of the first image 30 (i.e., the x-axis of the first image 30), wherein "n" and "m" are the length of the indicated image as expressed as the number of pixels (or other dimensions on other exemplary embodiments) that comprise the length of the indicated image. If the offset angle θ is known, each transverse slice (also known as an "axial slice" by some radiologists) of the volume 61 creates an epipolar plane comprising voxels that are back projected from the pixels that comprise the two epipolar lines. In this manner, projecting spatial data 43 from the first image 30 of the subject orthopedic element 100 and the spatial data 43 from the second image 50 of the subject orthopedic element 100 defines the volume data 75. Using this volume data 75, the 3D representation can be reconstructed using epipolar geometric principles as discussed above; the 3D representation is consistent geometrically with the information in the input images 30, 50.

In exemplary systems and methods for identifying an orthopedic element and/or a component of an endoprosthetic implant and in exemplary systems and methods for ascertaining a position of an orthopedic element and a component of an endoprosthetic implant in space using a deep learning network, wherein the deep learning network is a CNN, a detailed example of how the CNN can be structured and trained is provided. All architecture of CNNs are considered to be within the scope of this disclosure. Common CNN architectures include by way of example, LeNet, GoogLeNet, AlexNet, ZFNet, ResNet, and VGGNet.

Preferably, the methods disclosed herein may be implemented on a computer platform (see 1600) having hardware such as one or more central processing units (CPU), a random access memory (RAM), and input/output (I/O) interface(s).

Figure 10:
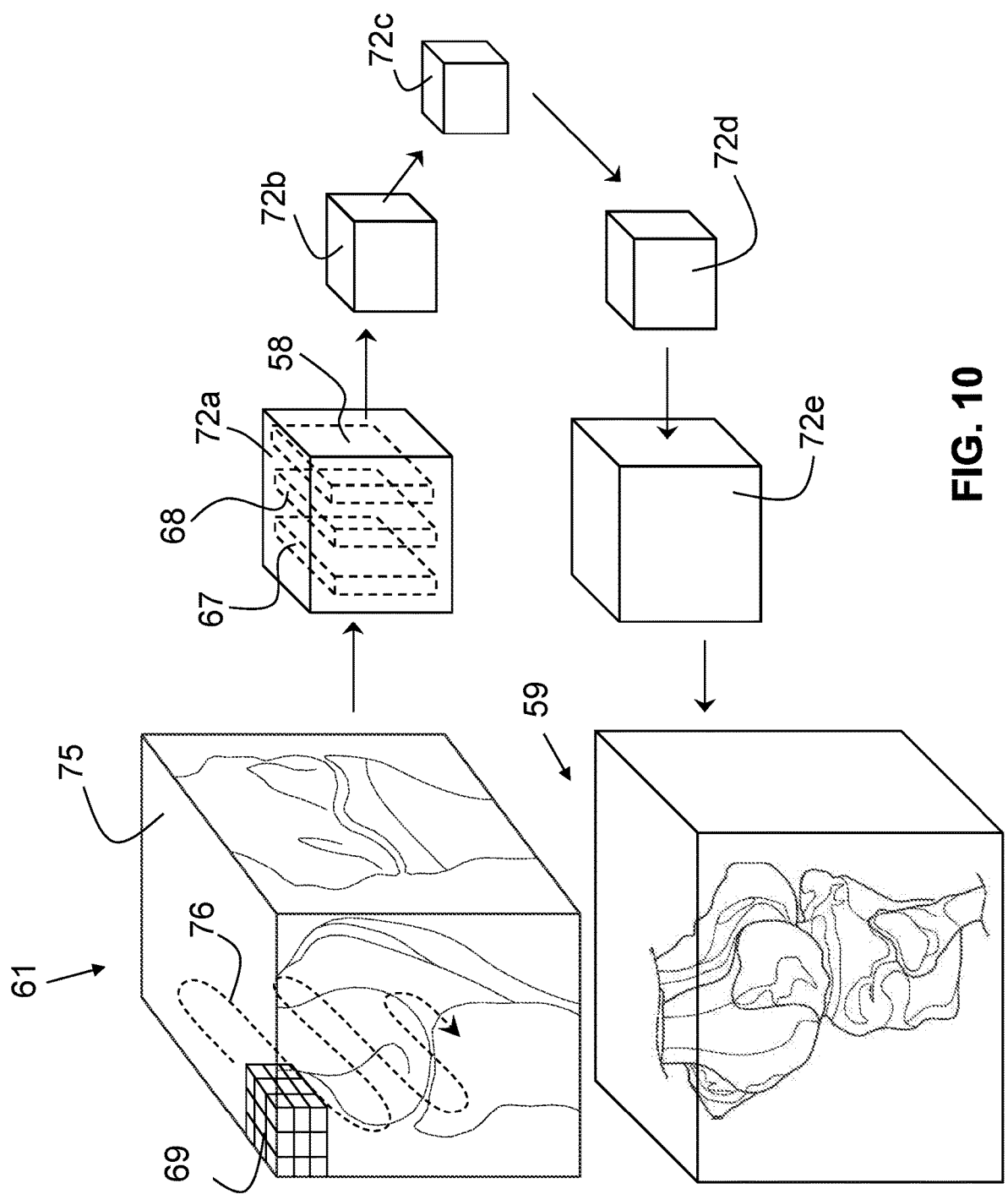
FIG. 10 is a schematic representation depicting how a convolutional neural network ("CNN") type deep learning network can be used to identify features (e.g., anatomical landmarks), including the surface of a subject orthopedic element.

FIG. 10 is a schematic representation of a CNN that illustrates how the CNN can be used to identify the edges of a subject orthopedic element 100. Without being bound by theory, it is contemplated that a CNN may be desirable for reducing the size of the volume data 75 without losing features that are necessary to identify the desired orthopedic element 100 or its surface topography. The volume data 75 of the multiple back projected input images 30, 50 is a multidimensional array that can be known as an "input tensor." This input tensor comprises the input data (which is the volume data 75 in this example) for the first convolution. A filter (also known as a kernel 69) is shown disposed in the volume data 75. The kernel 69 is a tensor (i.e., a multidimensional array) that defines a filter or function (this filter or function is sometimes known as the "weight" given to the kernel). In the depicted embodiment, the kernel tensor 69 is three dimensional. The filter or function that comprises the kernel 69 can be programed manually or learned through the CNN, RNN, or other deep learning network. In the depicted embodiment, the kernel 69 is a 3×3×3 tensor although all tensor sizes and dimensions are considered to be within the scope of this disclosure, provided that the kernel tensor size is less than the size of the input tensor.

Each cell or voxel of the kernel 69 has a numerical value. These values define the filter or function of the kernel 69. A convolution or cross-correlation operation is performed between the two tensors. In FIG. 10, the convolution is represented by the path 76. The path 76 that the kernel 69 follows is a visualization of the mathematical convolution operation. Following this path 76, the kernel 69 eventually and sequentially traverses the entire volume 61 of the input tensor (e.g., the volume data 75). The goal of this operation is to extract features from the input tensor.

Convolution layers 72 typically comprise one or more of the following operations: a convolution stage 67, a detector stage 68, and a pooling stage 58. Although these respective operations are represented visually in the first convolution layer 72a in FIG. 10, it will be appreciated that the subsequent convolution layers 72b, 72c, etc. may also comprise one or more or all of the convolution stage 67, detector stage 68, and pooling layer 58 operations or combinations or permutations thereof. Furthermore, although FIG. 10, depicts five convolution layers 72a, 72b, 72c, 72d, 72e of various resolutions, it will be appreciated that more or less convolution layers may be used in other exemplary embodiments.

In the convolution stage 67, the kernel 69 is sequentially multiplied by multiple patches of pixels in the input data (i.e., the volume data 75 in the depicted example). The patch of pixels extracted from the data is known as the receptive field. The multiplication of the kernel 69 and the receptive field comprises an element-wise multiplication between each pixel of the receptive field and the kernel 69. After multiplication, the results are summed to form one element of a convolution output. This kernel 69 then shifts to the adjacent receptive field and the element-wise multiplication operation and summation continue until all the pixels of the input tensor have been subjected to the operation.

Until this stage, the input data (e.g., the volume data 75) of the input tensor has been linear. To introduce nonlinearity to this data, a nonlinear activation function is then employed. Use of such a non-linear function marks the beginning of the detector stage 68. A common non-linear activation function is the Rectified Linear Unit function ("ReLU"), which is given by the function:

$$ReLU(x) = \begin{Bmatrix} 0, \text{ if } x < 0 \\ x, \text{ if } x \geq 0 \end{Bmatrix}$$

When used with bias, the non-linear activation function serves as a threshold for detecting the presence of the feature extracted by the kernel 69. For example, applying a convolution or a cross-correlation operation between the input tensor and the kernel 69, wherein the kernel 69 comprises a low level edge filter in the convolution stage 67 produces a convolution output tensor. Then, applying a non-linear activation function with a bias to the convolution output tensor will return a feature map output tensor. The bias is sequentially added to each cell of the convolution output tensor. For a given cell, if the sum is greater than or equal to 0 (assuming ReLU is used in this example), then the sum will be returned in the corresponding cell of the feature map output tensor. Likewise, if the sum is less than 0 for a given cell, then the corresponding cell of the feature map output tensor will be set to 0. Therefore, applying non-linear activation functions to the convolution output behaves like a threshold for determining whether and how closely the convolution output matches the given filter of the kernel 69. In this manner, the non-linear activation function detects the presence of the desired features from the input data (e.g., the volume data 75 in this example).

All non-linear activation functions are considered to be within the scope of this disclosure. Other examples include the Sigmoid, Tan H, Leaky ReLU, parametric ReLU, Softmax, and Switch activation functions.

However, a shortcoming of this approach is that the feature map output of this first convolutional layer 72a records the precise position of the desired feature (in the above example, an edge). As such, small movements of the feature in the input data will result in a different feature map. To address this problem and to reduce computational power, down sampling is used to lower the resolution of the input data while still preserving the significant structural elements. Down sampling can be achieved by changing the stride of the convolution along the input tensor. Down sampling is also achieved by using a pooling layer 58.

Valid padding may be applied to reduce the dimensions of the convolved tensor (see 72b) compared to the input tensor (see 72a). A pooling layer 58 is desirably applied to reduce the spatial size of the convolved data, which decreases the computational power required to process the data. Common pooling techniques, including max pooling and average pooling may be used. Max pooling returns the maximum value of the portion of the input tensor covered by the kernel 69, whereas average pooling returns the average of all the values of the portion of the input tensor covered by the kernel 69. Max pooling can be used to reduce image noise.

In certain exemplary embodiments, a fully connected layer can be added after the final convolution layer 72e to learn the non-linear combinations of the high level features (such as for example, the profile of an imaged natural acetabulum 108, the profile of a reamed acetabulum 109, or the surface topology of the orthopedic element) represented by the output of the convolutional layers.

When used on an orthopedic element 100, the above description of a CNN type deep learning network is one example of how a deep learning network can be "configured to identify" an orthopedic element 100 to define an "identified orthopedic element" 100a.

The top half of FIG. 10 represents compression of the input volume data 75, whereas the bottom half represents decompression until the original size of the input volume data 75 is reached. The output feature map of each convolution layer 72a, 72b, 72c, etc. is used as the input for the following convolution layer 72b, 72c, etc. to enable progressively more complex feature extraction. For example, the first kernel 69 may detect edges, a kernel in the first convolution layer 72b may detect a collection of edges in a desired orientation, a kernel in a third convolution layer 72c may detect a longer collection of edges in a desired orientation, etc. This process may continue until the entire profile of the desired orthopedic element 100 is detected and identified by a downstream convolution layer 72.

The bottom half of FIG. 10 up-samples (i.e., expands the spatial support of the lower resolution feature maps. A de-convolution operation is performed in order to increase the size of the input for the next downstream convolutional layer (see 72c, 72d, 72e). For the final convolution layer 72e, a convolution can be employed with a 1×1×1 kernel 69 to produce a multi-channel output volume 59 that is the same size as the input volume 61. Each channel of the multi-channel output volume 59 can represent a desired extracted high level feature. This can be followed by a Softmax activation function to detect the desired orthopedic elements 100. For example, the depicted embodiment may comprise five output channels numbered 0, 1, 2, 3, 4, wherein channel 0 represents identified background volume, channel 1 represents the identified proximal femur 105, channel 2 represents the identified reamed acetabulum 111, channel 3 represents the identified acetabular component 103, and channel 4 represents the identified femoral component 104.

It will be appreciated that less output channels or more output channels may be used in other exemplary embodiments. It will also be appreciated that the provided output channels may represent different orthopedic elements 100 and components of endoprosthetic implants than those listed here.

For example, in exemplary embodiments in which the system is configured to identify an orthopedic element 100, wherein the orthopedic element 100 is the inner cortical wall 120 of the proximal femur 105 and in which the system is configured to identify a component of an endoprosthetic implant, wherein the component of the endoprosthetic implant is a trial component construct, the exemplary embodiment may comprise three output channels numbered 0, 1, 2, wherein channel 0 represents identified background volume, channel 1 represents the inner cortical wall 120 of the proximal femur 105, and channel 2 represents the identified femoral component 104. A "trial component construct" as used in the above example, when the trial component construct describes a construct to be used in the proximal femur 105 can include a broach, trial neck, and trial head assembly, or a trial stem.

In exemplary embodiments in which the system is configured to identify an orthopedic element 100, wherein the orthopedic element 100 is the reamed acetabulum 111 of the pelvis 110 and in which the system is configured to identify a component of an endoprosthetic implant, wherein the component of the endoprosthetic implant is an acetabular component 103 or a trial acetabular component, the exemplary embodiment may comprise three output channels numbered 0, 1, 2, wherein channel 0 represents identified background volume, channel 1 represents the reamed acetabulum 111 of the pelvis 110, and channel 2 represents the an acetabular component 103 or the trial acetabular component.

Such exemplary embodiments can optionally comprise additional output channels, such as an output channel that represents the outer wall of the proximal femur 105. Other output channels can be used to output the abduction angle $\alpha$ and the anteversion angle $v$ respectively of the identified component of an endoprosthetic implant relative to the identified orthopedic element 100a in which the component of the endoprosthetic implant sits. Still other output channels may be used to output (by way of non-limiting examples) a determined size dimension of the identified orthopedic element, a recommended component type/product model of an endoprosthetic implant, a recommended component size of an endoprosthetic implant, a "best fit" output of a recommend component or of a recommended component size relative to the dimensions of the inner cortical wall 120, an alignment calculation of the longitudinal axis of the femoral component 104, a trial component construct relative to an anatomical axis of the proximal femur 105, the calculated center of the acetabulum, or the alignment of a longitudinal axis of the neck of the femoral component 104 relative to the center of the artificial femoral head 113. Combinations of any of the foregoing are considered to be within the scope of this disclosure.

When used on a component of an endoprosthetic implant or subcomponents thereof, the above description of a CNN type deep learning network is one example of how a deep learning network can be "configured to identify" a component of an endoprosthetic implant (or subcomponents thereof) to define an identified component of the endoprosthetic implant. When used on an endoprosthetic implant, the above description of a CNN type deep learning network is one example of how a deep learning network can be "configured to identify" an endoprosthetic implant to define an "identified endoprosthetic implant." It will be further understood that when applied to multiple orthopedic elements, multiple components of endoprosthetic implants, multiple endoprosthetic implants, or combinations thereof, the above description of a CNN type deep learning network is one example of how a deep learning network can be "configured to identify" multiple orthopedic elements, multiple components of endoprosthetic implants, subcomponents thereof, multiple endoprosthetic implants, or combinations thereof as the case may be. Other deep learning network architectures known or readily ascertainable by those having ordinary skill in the art are also considered to be within the scope of this disclosure.

In exemplary embodiments, select output channels comprising output volume data 59 of the desired orthopedic element 100 can be used to generate a modeled orthopedic element 100b, a modeled component of an endoprosthetic implant (e.g., an acetabular cup 106, a femoral stem 115, etc.). In certain exemplary embodiments, the modeled orthopedic element 100b is a computer model. In other exemplary embodiments, the modeled orthopedic element 100b is a physical model.

Although the above example described the use of a three dimensional tensor kernel 69 to convolve the input volume data 75, it will be appreciated that the general model described above can be used with 2D spatial data 43 from any of the calibrated input images 30, 50, 70. In other exemplary embodiments, a machine learning algorithm (i.e., a deep learning network (such as for example, a CNN)) can be used after calibration of the imaging machine 1800 but before 2D to 3D reconstruction. That is, the CNN can be used to detect features (e.g., anatomical landmarks) of a subject orthopedic element 100 from the first reference frame 30a, the second reference frame 50a, or the third reference frame 70a of the 2D input images 30, 50, 70. In exemplary embodiments, a CNN may be used to identify high level orthopedic elements (e.g., the proximal femur 105 and a portion of the surface topology of the subject orthopedic element 100), components of an endoprosthetic implant (e.g., the acetabular cup 106, femoral stem 115, etc.) or the endoprosthetic implant itself (e.g. the hip endoprosthetic implant 102) from the 2D input images 30, 50, 70. The CNN may then optionally apply a mask or an outline to the detected orthopedic element 100, component of an endoprosthetic implant, or the endoprosthetic implant itself. It is contemplated that if the imaging machine 1800 is calibrated, and if the CNN identified multiple corresponding image points (e.g., $X_L$, $X_R$) of features between the at least two input images 30, 50, then the transformation matrices between the reference frames 30a, 50a of a subject orthopedic element 100, component of an endoprosthetic implant, or the endoprosthetic implant itself can be used to align the multiple corresponding image points in 3D space. In this manner, the position of the points in 3D space can be determined to correspond to a set of coordinates in 3D space. In this manner, the 3D points can be said to be "mapped" to spatial data. A deep learning network that is capable of modeling this relationship in this manner or in other manners developed by the deep learning network can be said to be "configured to map" the identified orthopedic element, the identified component of the endoprosthetic implant, and/or the endoprosthetic implant itself (as the case may be) to spatial data ascertained by the first input image 30 and the second input image 50 (and optionally the third input image 70 or further input images or 'new' refreshing images) to thereby determine the position of the identified orthopedic element 100a, the identified component of the endoprosthetic implant, and/or the endoprosthetic implant itself (as the case may be) in three dimensional space.

In embodiments wherein any of the first input image 30, the second input image 50, or the third input image 70 are radiographic X-ray images (including, but not limited to fluoroscopic radiographic images), training a CNN can present several challenges. By way of comparison, CT scans typically produce a series of images of the desired volume. Each CT image that comprises a typical CT scan can be imagined as a segment of the imaged volume. From these segments, a 3D model can be created relatively easily by adding the area of the desired element as the element is depicted in each successive CT image. The modeled element can then be compared with the data in the CT scan to ensure accuracy. One drawback of CT scans is that CT scans expose the patient to excessive amounts of radiation (about seventy times the amount radiation of one traditional radiograph).

By contrast, radiographic imaging systems typically do not generate sequential images that capture different segments of the imaged volume; rather, all of the information of the image is flattened on the 2D plane. Additionally, because a single radiographic image 30 inherently lacks 3D data, it is difficult to check the model generated by the epipolar geometry reconstruction technique described above with the actual geometry of the target orthopedic element 100. To address this issue, the CNN can be trained with CT images, such as digitally reconstructed radiograph ("DRRs") images. By training the deep learning network in this way, the deep learning network can develop its own weights (e.g., filters) for the kernels 69 to identify a desired orthopedic element 100 or surface topography of a subject orthopedic element 100. Because X-ray radiographs have a different appearance than DRRs, image-to-image translation can be performed to render the input X-ray images to have a DRR-style appearance. An example image-to-image translation method is the Cycle-GAN image translation technique. In embodiments in which image-to-image style transfer methods are used, the style transfer method is desirably used prior to inputting the data into a deep learning network for feature detection.

The above examples are provided for illustrative purposes and are in no way intended to limit the scope of this disclosure. All methods for generating a 3D model of the subject orthopedic element 100 from 2D radiographic images of the same subject orthopedic element 100 taken from at least two transverse positions (e.g., 30a, 50a) are considered to be within the scope of this disclosure.

Determining the metes and bounds of a particular identified orthopedic element 100a component of the endoprosthetic implant, and/or the endoprosthetic implant, component of the endoprosthetic implant, and/or the endoprosthetic implant itself and their precise coordinates in 3D space, permits the position of the identified orthopedic element 100a, component of the endoprosthetic implant, and or the endoprosthetic implant, component of the endoprosthetic implant, and or the endoprosthetic implant to be known while bypassing the limited field of view offered to the surgeon through the main incision. If the position of the identified orthopedic element 100a is known, and if the position of the identified component of the endoprosthetic implant is known, then this information can be used to check against the desired alignment parameters of the implant component relative to the identified orthopedic element 100a into which the implant component is installed (e.g. an acetabular shell 106 installed into a reamed acetabulum 111, a femoral stem 115 installed into the intramedullary canal of the proximal femur 105, etc.).

Likewise, if the position of a first component of an endoprosthetic implant (e.g., the acetabular component) is known relative to a second component of the endoprosthetic implant (e.g., the femoral component) in three dimensions, then the surgeon can use the exemplary systems and methods described herein to evaluate the placement and therefore the alignment of the first component relative to the second component. The surgeon may re-image the operative area to update the position of the first component relative to the second component at subsequent time intervals until the surgeon is satisfied with the alignment. It is contemplated that such alignment may be performed intraoperatively to mitigate the problems of misaligned components of multi-component endoprosthetic implants.

In certain exemplary embodiments that comprise using a deep learning network to add a mask or an outline to the detected 2D orthopedic element 100 from the respective input images 30, 50, 70 only the 2D masks or outlines of the identified orthopedic element 100 component of the endoprosthetic implant, and/or the endoprosthetic implant can be sequentially back projected in the manner described with reference to FIGS. 7 and 8 supra to define a volume 61 of the identified orthopedic element 100, component of the endoprosthetic implant, and/or the endoprosthetic implant. In this exemplary manner, a modeled orthopedic element 100b, modeled component of the endoprosthetic implant, and/or a modeled endoprosthetic implant may be generated.

Figure 11:
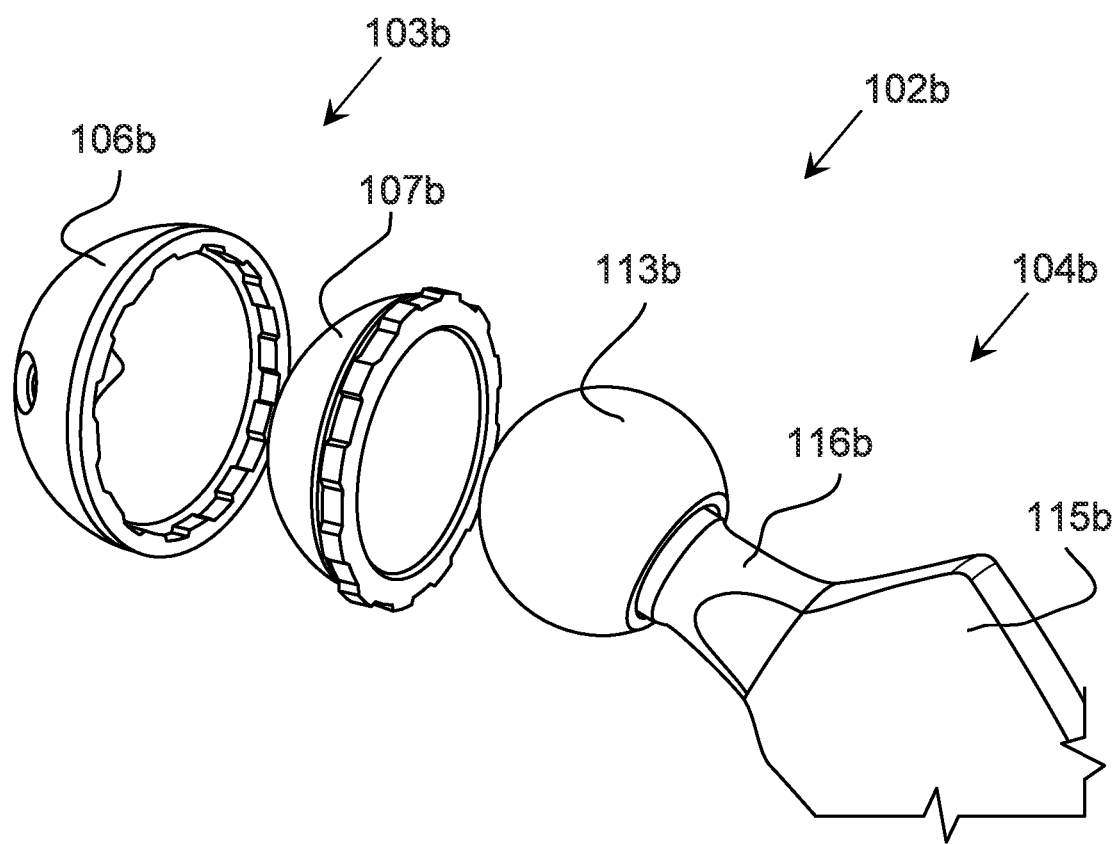
FIG. 11 is an exploded view of a modeled endoprosthetic implant.

FIG. 11 is a close up of a modeled endoprosthetic implant 102b comprising several modeled endoprosthetic implant components, namely, a modeled acetabular component 103b and a modeled femoral component 104b. The modeled acetabular component 103b comprises a modeled acetabular shell 106b and a modeled acetabular liner 107b. The modeled femoral component 104b comprises a modeled femoral stem 115b, modeled femoral stem neck 116b, and modeled artificial femoral head 113b.

An exemplary system or method may further comprise calculating a center of the acetabulum. Such an exemplary system or method may still further comprise aligning a longitudinal rotational axis of a femoral stem implant with the center of the acetabulum. In still other exemplary systems or methods, the longitudinal axis of the femoral stem 115 can be aligned (i.e., co-linear) with the longitudinal axis of the femur 105. In still other exemplary systems and methods, the rotational axis of the neck of the femoral stem 115 can be aligned with the center of the artificial femoral head 113. In still other exemplary systems and methods, the position of the artificial head 113 can be aligned (e.g., vertically) with the pre-diseased natural femoral head based upon input images of the natural femoral head. In such exemplary embodiments, the longitudinal axis of the femoral stem 115 is desirably co-linear with the anatomical axis of the femur 105 and the femoral stem 115 is desirably disposed at an anteversion angle ν in the range of about 10° to about 30°, desirably about 15° to about 25°.

A computer platform, having hardware such as one or more central processing units (CPU), a random access memory (RAM), and input/output (I/O) interface(s) can receive at least two 2D radiographic images taken at different orientations along a transverse plane. The orientations can be orthogonal to each other (i.e., the first reference frame has an offset angle θ of 90° relative to the second reference frame). However, in embodiments in which the orthopedic elements 100 comprise a hip joint 101, at least three 2D radiographic input images can be desirable to avoid interference from the contralateral acetabulum. In such exemplary embodiments, the offset angle θ can be desirably 45° among adjacent reference frames. Other obtuse or acute offset angles θ can be used in other exemplary embodiments.

Referring to FIG. 12, an exemplary system for ascertaining a position of an orthopedic element 100 and a component of an endoprosthetic implant in space can comprise: a tissue-penetrating imaging machine 1800 (such as a radiographic imaging machine, fluoroscopy machine, etc.) comprising an emitter 21 and a detector 33, wherein the detector 33 of the radiographic imaging machine 1800 captures a first input image 30 (FIGS. 8 and 9A) in a first transversion position 30a (FIGS. 8 and 9A) and a second input image 50 (FIGS. 8 and 9B) in a second transverse position 50a (FIGS. 8 and 9B), wherein the first transverse position 30a is offset from the second transverse position 50a by an offset angle θ (FIG. 8). In exemplary embodiments involving at least three input images, the detector 33 of the radiographic imaging machine 1800 captures a third input image 70 (FIGS. 8 and 9C) in a third transverse position 70a (FIGS. 8 and 9C), wherein the third transverse position 70a is offset from the second transverse position 50a and the first transverse position 30a by two separate offset angles θ1, θ2.

The exemplary system can further comprise a transmitter 29 (FIG. 12), and a computational machine 1600 (see FIG. 13 for further details) wherein the transmitter 29 transmits the first input image 30 and the second input image 50 (and optionally the third input image 70 if present) from the detector 33 to the computational machine 1600, and wherein the computational machine 1600 is configured to identify an orthopedic element 100a, component of an endoprosthetic implant, subcomponent of a component of an endoprosthetic implant, or the endoprosthetic implant itself using one of the deep learning methods discussed herein. It will be appreciated that the exemplary systems disclosed herein can be used pre-operatively, intraoperatively, and/or post operatively.

In certain exemplary embodiments, an exemplary system may further comprise a display 19.

FIG. 12 is a schematic representation of an exemplary system comprising a radiographic imaging machine 1800 comprising an X-ray source 21, such as an X-ray tube, a filter 26, a collimator 27, and a detector 33. In FIG. 12, the radiographic imaging machine 1800 is shown from the top down. The depicted radiographic imaging machine 1800 is a type of tissue-penetrating imaging machine. A patient 1 is disposed between the X-ray source 21 and the detector 33. The radiographic imaging machine 1800 may be mounted on a rotatable gantry 28. The radiographic imaging machine 1800 may take a first radiographic input image 30 of the patient 1 from a first reference frame 30a. The gantry 28 may then rotate the radiographic imaging machine 1800 by an offset angle. The radiographic imaging machine 1800 may then take the second radiographic input image 50 from the second reference frame 50a. It will be appreciated that other exemplary embodiments can comprise using multiple input images taken at multiple offset angles θ. For example, in a hip arthroplasty, the radiographic imaging machine 1800 may be further rotated (or the patient rotated) to capture a third radiographic input images 70 from a third reference frame 70a. In such embodiments, the offset angle may be less than or greater than 90° between adjacent input images.

It will be appreciated that the offset angle need not be exactly 90 degrees in every embodiment. An offset angle having a value within a range that is plus or minus 45 degrees is contemplated as being sufficient. In other exemplary embodiments, an operator may take more than two images of the orthopedic element using a radiographic imaging technique. It is contemplated that each subsequent image after the second image can define a subsequent image reference frame. For example, a third image can define a third reference frame, a fourth image can define a fourth reference frame, the $n^{th}$ image can define an $n^{th}$ reference frame, etc.

In other exemplary embodiments comprising three input images and three distinct reference frames, each of the three input images may have an offset angle θ of about 60 degrees relative to each other. In some exemplary embodiments comprising four input images and four distinct reference frames, the offset angle θ may be 45 degrees from an adjacent reference frame. In an exemplary embodiment comprising five input images and five distinct reference frames, the offset angle θ may be about 36 degrees from the adjacent reference frame. In exemplary embodiments comprising n images and n distinct reference frames, the offset angle θ can be 180/n degrees.

It is further contemplated that embodiments involving multiple images, especially more than two images do not necessarily have to have regular and consistent offset angles. For example, an exemplary embodiment involving four images and four distinct reference frames may have a first offset angle at 85 degrees, a second offset angle at 75 degrees, a third offset angle at 93 degrees, and a fourth offset angle at 107 degrees.

A transmitter 29 then transmits the first input image 30 and the second input image 50 to a computational machine 1600. The computational machine 1600 can use a deep learning network to identify an orthopedic element 100a, component of an endoprosthetic implant, subcomponent of a component of an endoprosthetic implant, or the endoprosthetic implant itself in any manner that is consistent with this disclosure.

FIG. 12 also depicts another embodiment in which the output data from the computational machine 1600 is transmitted to a display 19. A display 19 can depict a modeled endoprosthetic implant 102b. The display may optionally display any of the items identified by the exemplary systems and methods described herein, including but not limited to the identified endoprosthetic implant, component of the endoprosthetic implant or subcomponent thereof, or one or more orthopedic elements. In exemplary embodiments, it is contemplated that the identified component of the endoprosthetic implant, or the representative model of the component of the endoprosthetic implant can be superimposed on the identified orthopedic element into which the component of the endoprosthetic implant will be seated (e.g., the femoral component and the proximal femur respectively). The superimposition can be calculated and displayed using the mapped spatial data of the respective identified elements (e.g., the component of the endoprosthetic implant and the orthopedic element into which the component of the endoprosthetic implant will be seated).

In this manner, the surgeon and others in the operating room can have a near real time visualization of the component of the endoprosthetic implant and the target orthopedic element in three dimensions and their alignment relative to one another.

Furthermore, because the spatial data of an identified component of the endoprosthetic implant and because the spatial data of the identified orthopedic element can be obtained from exemplary systems described herein, the degree of alignment can be calculated and further displayed on a display 19 in exemplary system embodiments. For example, a calculated abduction angle α of the identified component of the endoprosthetic implant can displayed on a display. By way of another example, calculated anteversion angle ν of the identified component of the endoprosthetic implant is displayed on a display 19. By way of yet another example, the vertical position of the artificial head 113 can be displayed and superimposed on a reconstructed 3D image of the natural femoral head (see 126) of the operative hip based upon preoperative planning input images 30, 50, 70. By way of still yet another example, the display 19 may optionally display a "best fit" percentage in which a percentage reaching or close to 100% reflects the alignment of an identified component of an endoprosthetic implant (e.g., a femoral component 104) relative to a reference orthopedic element.

For example, in embodiments wherein the identified component of an endoprosthetic implant is the femoral component 104, the reference orthopedic element can be the native proximal femur 105 of the operative joint that was identified and reconstructed in accordance with any of the embodiments of this disclosure from preoperative planning input images. In such exemplary embodiments, the alignment best fit percentage can consider the anteversion angle ν of the identified femoral component 104, the varus-valgus position of the femoral stem 115 of the femoral component 104 relative to the anatomical axis of the femur 105, the anterior-posterior angle of the femoral stem 115 in the intramedullary canal of the femur 105 of the operative hip joint 101 and the vertical, horizontal, and anterior-posterior position of the artificial femoral head 113 relative to the natural femoral head (see 126) of the operative hip joint 101 prior to resection. Combinations of any of the forgoing embodiments of what can be displayed on the display 19 are considered to be within the scope of this disclosure.

In embodiments in which the identified component of an endoprosthetic implant is a femoral component of a hip implant and in which the identified orthopedic element is the proximal femur into which the femoral component will be inserted and seated, exemplary systems may display the varus or valgus angle of the longitudinal axis of the femoral component relative to the anatomical axis of the femur (i.e., the central axis of the femur extending through the intramedullary canal of the femur).

Exemplary systems may further comprise one or more databases. One or more databases can comprise a list of types of components of an endoprosthetic implant and associated component size dimensions for the types of components (e.g., different product models of a particular component) in the list of components of the endoprosthetic implant. In exemplary embodiments, a database can comprise a list of sizes for components of one particular type of component of an endoprosthetic implant.

The computational machine can compare the dimensions of the identified component of an endoprosthetic implant with the values stored in the database. The computation machine may then select or display a recommended type of component and/or a recommended size of a particular component from the values stored in the database based upon how closely the dimensions of the identified component of the endoprosthetic implant match the dimensions of the values stored in the database. In this way, a computational machine 1600 can be said to "configured to select" a recommended type of component of an endoprosthetic implant based on the determined size dimensions of the identified orthopedic element in three dimensional space. Likewise, in this way, a computational machine 1600 can be said to be "configured to recommend a size of a component of an endoprosthetic implant" based on the determined size dimensions of the identified orthopedic element in three dimensional space.

This display 19 may take the form of a screen. In other exemplary embodiments, the display 19 may comprise a glass or plastic surface that is worn or held by the surgeon or other people in the operation theater. Such a display 19 may comprise part of an augmented reality device, such that the display shows the 3D model in addition to the wearer's visual field. In certain embodiments, such a 3D model can be superimposed on the actual operative joint. In yet other exemplary embodiments, the 3D model can be "locked" to one or more features of the operative orthopedic element 100, thereby maintaining a virtual position of the 3D model relative to the one or more features of the operative orthopedic element 100 independent of movement of the display 19. It is still further contemplated that the display 19 may comprise part of a virtual reality system in which the entirety of the visual field is simulated.

Although X-ray radiographs from an X-ray imaging system may be desirable because X-ray radiographs are relatively inexpensive compared to CT scans and because the equipment for some X-ray imaging systems, such as a fluoroscopy system, are generally sufficiently compact to be used intraoperatively, nothing in this disclosure limits the use of the 2D images to X-ray radiographs unless otherwise expressly claimed, nor does anything in this disclosure limit the type of imaging system to an X-ray imaging system. Other 2D images can include by way of example: CT-images, CT-fluoroscopy images, fluoroscopy images, ultrasound images, positron emission tomography ("PET") images, and MRI images. Other imaging systems can include by way of example: CT, CT-fluoroscopy, fluoroscopy, ultrasound, PET, and MRI systems.

Preferably, the exemplary methods can be implemented on a computer platform (e.g., a computational machine 1600) having hardware such as one or more central processing units (CPU), a random access memory (RAM), and input/output (I/O) interface(s). An example of the architecture for an example computational machine 1600 is provided below with reference to FIG. 7.

Figure 13:
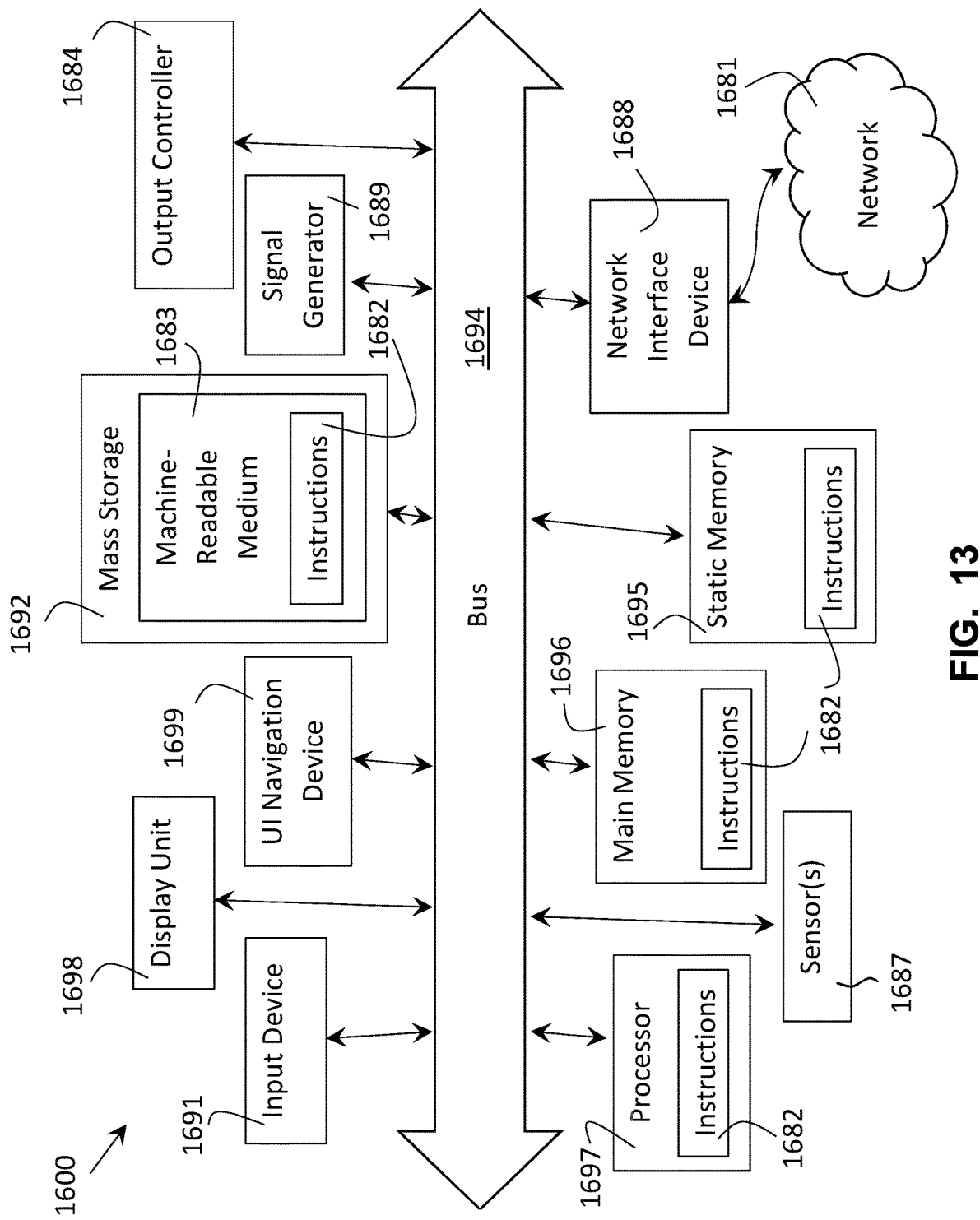
FIG. 13 is a schematic representation of a system configured to generate a model of an orthopedic element and to align components of endoprosthetic implant components using two or more tissue penetrating, flattened, input images taken of the same subject orthopedic element from calibrated detectors at an offset angle.

FIG. 13 generally depicts a block diagram of an exemplary computational machine 1600 upon which one or more of the methods discussed herein may be performed in accordance with some exemplary embodiments. In certain exemplary embodiments, the computational machine 1600 can operate on a single machine. In other exemplary embodiments, the computational machine 1600 can comprise connected (e.g., networked) machines. Examples of networked machines that can comprise the exemplary computational machine 1600 include by way of example, cloud computing configurations, distributed hosting configurations, and other computer cluster configurations. In a networked configuration, one or more machines of the computational machine 1600 can operate in the capacity of a client machine, a server machine, or both a server-client machine. In exemplary embodiments, the computational machine 1600 can reside on a personal computer ("PC"), a mobile telephone, a tablet PC, a web appliance, a personal digital assistant ("PDA"), a network router, a bridge, a switch, or any machine capable of executing instructions that specify actions to be undertaken by said machine or a second machine controlled by said machine.

Example machines that can comprise the exemplary computational machines 1600 can include by way of example, components, modules, or like mechanisms capable of executing logic functions. Such machines may comprise tangible entities (e.g., hardware) that is capable of carrying out specified operations while operating. As an example, the hardware may be hardwired (e.g., specifically configured) to execute a specific operation. By way of example, such hardware may have configurable execution media (e.g., circuits, transistors, logic gates, etc.) and a computer-readable medium having instructions, wherein the instructions configure the execution media to carry out a specific operation when operating. The configuring can occur via a loading mechanism or under the direction of the execution media. The execution media selectively communicate to the computer-readable medium when the machine is operating. By way of an example, when the machine is in operation, the execution media may be configured by a first set of instructions to execute a first action or set of actions at a first point in time and then reconfigured at a second point in time by a second set of instructions to execute a second action or set of actions.

The exemplary computational machine 1600 may include a hardware processor 1697 (e.g., a CPU, a graphics processing unit ("GPU"), a hardware processor core, or any combination thereof, a main memory 1696 and a static memory 1695, some or all of which may communicate with each other via an interlink (e.g., a bus) 1694. The computational machine 1600 may further include a display unit 1698, an input device 1691 (preferably an alphanumeric or character-numeric input device such as a keyboard), and a user interface ("UP") navigation device 1699 (e.g., a mouse or stylus). In an exemplary embodiment, the input device 1691, display unit 1698, and UI navigation device 1699 may be a touch screen display. In exemplary embodiments, the display unit 1698 may include holographic lenses, glasses, goggles, other eyewear, or other AR or VR display components. For example, the display unit 1698 may be worn on a head of a user and may provide a heads-up-display to the user. The input device 1691 may include a virtual keyboard (e.g., a keyboard displayed virtually in a virtual reality ("VR") or an augmented reality ("AR") setting) or other virtual input interface.

The computational machine 1600 may further include a storage device (e.g., a drive unit) 1692, a signal generator 1689 (e.g., a speaker) a network interface device 1688, and one or more sensors 1687, such as a global positioning system ("GPS") sensor, accelerometer, compass, or other sensor. The computational machine 1600 may include an output controller 1684, such as a serial (e.g., universal serial bus ("USB"), parallel, or other wired or wireless (e.g., infrared ("IR") near field communication ("NFC"), radio, etc.) connection to communicate or control one or more ancillary devices.

The storage device 1692 may include a machine-readable medium 1683 that is non-transitory, on which is stored one or more sets of data structures or instructions 1682 (e.g., software) embodying or utilized by any one or more of the functions or methods described herein. The instructions 1682 may reside completely or at least partially, within the main memory 1696, within static memory 1695, or within the hardware processor 1697 during execution thereof by the computational machine 1600. By way of example, one or any combination of the hardware processor 1697, the main memory 1696, the static memory 1695, or the storage device 1692, may constitute machine-readable media.

While the machine-readable medium 1683 is illustrated as a single medium, the term, "machine readable medium" may include a single medium or multiple media (e.g., a distributed or centralized database, or associated caches and servers) configured to store the one or more instructions 1682.

The term "machine-readable medium" may include any medium that is capable of storing, encoding, or carrying instructions for execution by the computational machine 1600 and that cause the computational machine 1600 to perform any one or more of the methods of the present disclosure, or that is capable of storing, encoding, or carrying data structures used by or associated with such instructions. A non-limited example list of machine-readable media may include magnetic media, optical media, solid state memories, non-volatile memory, such as semiconductor memory devices (e.g., electronically erasable programmable read-only memory ("EEPROM"), electronically programmable read-only memory ("EPROM"), and magnetic discs, such as internal hard discs and removable discs, flash storage devices, magneto-optical discs, and CD-ROM and DVD-ROM discs.

The instructions 1682 may further be transmitted or received over a communications network 1681 using a transmission medium via the network interface device 1688 utilizing any one of a number of transfer protocols (e.g., internet protocol ("IP"), user datagram protocol ("UDP"), frame relay, transmission control protocol ("TCP"), hypertext transfer protocol ("HTTP"), etc.). Example communication networks may include a wide area network ("WAN"), a plain old telephone ("POTS") network, a local area network ("LAN"), a packet data network, a mobile telephone network, a wireless data network, and a peer-to-peer ("P2P") network. By way of example, the network interface device 1688 may include one or more physical jacks (e.g., Ethernet, coaxial, or phone jacks) or one or more antennas to connect to the communications network 1681.

By way of example, the network interface device 1688 may include a plurality of antennas to communicate wirelessly using at least one of a single-input multiple-output ("SIMO"), or a multiple-input single output ("MISO") methods. The phrase, "transmission medium" includes any intangible medium that is capable of storing, encoding, or carrying instructions for execution by the computational machine 1600, and includes analog or digital communications signals or other intangible medium to facilitate communication of such software.

Exemplary methods in accordance with this disclosure may be machine or computer-implemented at least in part. Some examples may include a computer-readable medium or machine-readable medium encoded with instructions operable to configure an electronic device to perform the exemplary methods described herein. An example implementation of such an exemplary method may include code, such as assembly language code, microcode, a higher-level language code, or other code. Such code may include computer readable instructions for performing various methods. The code may form portions of computer program products. A computational machine 1600 that can execute computer readable instructions for carrying out the methods and calculations of a deep learning network can be said to be "configured to run" a deep learning network. Further, in an example, the code may be tangibly stored on or in a volatile, non-transitory, or non-volatile tangible computer-readable media, such as during execution or other times. Examples of these tangible computer-readable media may include, but are not limited to, removable optical discs (e.g., compact discs and digital video discs), hard drives, removable magnetic discs, memory cards or sticks, include removable flash storage drives, magnetic cassettes, random access memories (RAMs), read only memories (ROMS), and other media.

It is further contemplated that the exemplary methods disclosed herein may be used for preoperative planning, intraoperative planning or execution, or postoperative evaluation of the implant placement and function.

An exemplary method for ascertaining a position of an orthopedic element in space can comprise: calibrating a radiographic imaging machine to determine a mapping relationship between image points and corresponding space coordinates to define spatial data; capturing a first image of an orthopedic element using a radiographic imaging technique, wherein the first image defines a first reference frame; capturing a second image of the orthopedic element using the radiographic imaging technique, wherein the second image defines a second reference frame, and wherein the first reference frame is offset from the second reference frame at an offset angle; using a deep learning network to detect the orthopedic element using the spatial data, the spatial data defining anatomical landmarks on or in the orthopedic element; using the deep learning network to apply a mask to the orthopedic element defined by an anatomical landmark; projecting the spatial data from the first image of the desired orthopedic element and the spatial data from the second image of the desired orthopedic element to define volume data, wherein the spatial data comprising image points disposed within a masked area of either the first image or the second image have a first value and wherein the spatial data comprising image points disposed outside of the masked area of either the first image or the second image have a second value, wherein the first value is different from the second value; applying the deep learning network to the volume data to generate a reconstructed three-dimensional model of the orthopedic element; and mapping the three-dimensional model of the orthopedic element to the spatial data.

In an exemplary embodiment, an exemplary method can further comprise using the deep learning network to perform a style transfer on the first image and the second image. In an exemplary embodiment, the style transfer converts the spatial data from the radiographic imaging technique into dynamic digital radiography data.

In an exemplary embodiment, the first value is a positive value.

In an exemplary embodiment, the second value is a negative value.

In an exemplary embodiment, the exemplary method further comprises projecting the reconstructed three-dimensional model on a display.

In an exemplary embodiment, the deep learning network comprises a convolutional neural network.

In an exemplary embodiment, the radiographic imaging technique is fluoroscopy.

In an exemplary embodiment, the method is performed intraoperatively.

In an exemplary embodiment, the orthopedic element is an acetabulum of a pelvis.

In an exemplary embodiment, the exemplary method further comprises calculating a center of the acetabulum.

In an exemplary embodiment, the exemplary method further comprises aligning a longitudinal rotational axis of a neck of the femoral stem (e.g., a component of an endoprosthetic implant) with the center of the acetabulum.

In an exemplary embodiment, the exemplary method further comprises aligning the acetabular shell (e.g., a component of an endoprosthetic implant) with the reamed acetabulum of the patient.

In an exemplary embodiment, the exemplary method further comprises aligning the femoral stem (e.g., a component of an endoprosthetic implant) in the intramedullary canal of the reamed proximal femur of the patient.

In an exemplary embodiment, the method further comprises aligning a longitudinal axis of a femoral stem (e.g., a component of an endoprosthetic implant) with the anatomical (i.e., center) axis of the femur.

An exemplary method for ascertaining a position of an orthopedic element in space comprises: calibrating a radiographic imaging machine to determine a mapping relationship between image points and corresponding space coordinates to define spatial data; using a radiographic imaging technique to capture a first image of an orthopedic element, wherein the first image defines a first reference frame; using the radiographic imaging technique to capture a second image of the orthopedic element, wherein the second image defines a second reference frame, and wherein the first reference frame is offset from the second reference frame at an offset angle; using a neural network to detect the orthopedic element using the spatial data, the spatial data defining an anatomical landmark on or in the orthopedic element; using the deep learning network to apply a mask to the orthopedic element defined by the anatomical landmark; projecting the spatial data from the first image of the desired orthopedic element and the spatial data from the second image of the desired orthopedic element to define volume data, wherein the spatial data comprising image points disposed within a masked area of either the first image or the second image have a positive value and wherein the spatial data comprising image points disposed outside of a masked area of either the first image or the second image have a negative value; applying the deep learning network to the volume data to generate a three-dimensional model of the orthopedic element; and mapping the three-dimensional model of the orthopedic element to the spatial data, wherein the orthopedic element is an acetabulum of a pelvis.

In an exemplary embodiment, the orthopedic element is resected or reamed during a surgical procedure.

In an exemplary embodiment, the method further comprises using the deep learning network to perform a style transfer on the first image and the second image.

In an exemplary embodiment, the style transfer converts the spatial data from the radiographic imaging technique into dynamic digital radiography data.

In an exemplary embodiment, the first value is a positive value.

In an exemplary embodiment, the second value is a negative value.

In an exemplary embodiment, the method further comprises projecting the reconstructed three-dimensional model on a display.

In an exemplary embodiment, the deep learning network comprises a convolutional neural network.

In an exemplary embodiment, the radiographic imaging technique is fluoroscopy.

In an exemplary embodiment, the method is performed intraoperatively.

In an exemplary embodiment, the method further comprises calculating a center of the acetabulum.

In an exemplary embodiment, the method further comprises aligning a longitudinal rotational axis of a neck of femoral stem rotationally with a center of the artificial femoral head and the longitudinal axis of the femoral stem with the anatomical axis of the intramedullary canal of the femur into which the femoral stem is placed.

In an exemplary embodiment, the exemplary method further comprises aligning the acetabular shell (e.g., a component of an endoprosthetic implant) with the reamed acetabulum of the patient.

In an exemplary embodiment, the exemplary method further comprises aligning the femoral stem (e.g., a component of an endoprosthetic implant) in the intramedullary canal of the reamed proximal femur of the patient.

In an exemplary embodiment, the method further comprises aligning a longitudinal axis of a femoral stem (e.g., a component of an endoprosthetic implant) with the anatomical axis of the femur into which the femoral stem is placed.

An exemplary system for ascertaining a position of an orthopedic element and a component of an endoprosthetic implant in space comprises: a tissue-penetrating imaging machine; a first input image, the first input image taken by the tissue penetrating imaging machine from a first reference frame, the first image depicting a calibration jig; a second input image, the second input image taken by the tissue penetrating imaging machine from a second reference frame, the second reference frame being offset from the first reference frame, the second image depicting the calibration jig; and a computational machine configured to run a deep learning network, wherein the deep learning network is configured to identify an orthopedic element and a component of an endoprosthetic implant to define an identified orthopedic element and an identified component of the endoprosthetic implant, and to map the identified orthopedic element and the identified component of the endoprosthetic implant to spatial data ascertained by the first input image and the second input image to thereby determine the position of the identified orthopedic element and the identified component of the endoprosthetic implant in three dimensional space.

In an exemplary embodiment, the system further comprises a third input image, the third input image is taken by the tissue penetrating imaging machine from a third reference frame, the third image depicting the calibration jig.

In an exemplary embodiment of the system, the deep learning network is further configured to identify multiple orthopedic elements and multiple components of the endoprosthetic implant to define multiple identified orthopedic elements and multiple identified components of the endoprosthetic implant.

In still further exemplary embodiments of the system, a first identified component of the multiple identified components of the endoprosthetic implant is an acetabular component of a hip endoprosthetic implant and a second identified component of the multiple identified components of the endoprosthetic implant is a femoral component of a hip endoprosthetic implant.

In an exemplary embodiment of the system, the identified component of the endoprosthetic implant is an acetabular shell and the identified orthopedic element is a reamed acetabulum proximate to the acetabular shell.

In an exemplary embodiment of the system, the identified component of the endoprosthetic implant is a femoral stem and the identified orthopedic element is an intramedullary canal of a femur proximate to the femoral stem.

In an exemplary embodiment of the system, the identified orthopedic element is modeled in three dimensions to define a modeled orthopedic element.

In an exemplary embodiment, the modeled orthopedic element is displayed on a display.

In an exemplary embodiment, the identified component of the endoprosthetic implant is modeled in three dimensions to define a modeled component of the endoprosthetic implant.

In an exemplary embodiment, the modeled component of the endoprosthetic implant is displayed on a display.

In an exemplary embodiment, a calculated abduction angle of the identified component of the endoprosthetic implant is displayed on a display.

In an exemplary embodiment, a calculated anteversion angle of the identified component of the endoprosthetic implant is displayed on a display.

An exemplary system for recommending a type of a component of an endoprosthetic implant to be surgically implanted into a patient, the system comprising: a tissue penetrating imaging machine; a first input image, the first input image taken by the tissue penetrating imaging machine from a first reference frame, the first image depicting a calibration jig; a second input image, the second input image taken by the tissue penetrating imaging machine from a second reference frame, the second reference frame being offset from the first reference frame, the second image depicting the calibration jig; a computational machine configured to run a deep learning network, wherein the deep learning network is configured to identify an orthopedic element to define an identified orthopedic element, and to map the identified orthopedic element to spatial data ascertained by the first input image and the second input image to thereby define determined size dimensions of the identified orthopedic element in three dimensional space; and a database, the database comprising a list of types of components of an endoprosthetic implant and associated component size dimensions for the types of components in the list of components of the endoprosthetic implant, wherein the computational machine is further configured to select a recommended type of component of an endoprosthetic implant based on the determined size dimensions of the identified orthopedic element in three dimensional space.

In an exemplary embodiment, the system further comprises a third input image, the third input image is taken by the tissue penetrating imaging machine from a third reference frame, the third image depicting the calibration jig.

In an exemplary embodiment, the identified orthopedic element is the internal geometry of a bone before or after reaming or before or after broaching.

In an exemplary embodiment, the computational machine is configured to run a best fit algorithm to select a recommended component of an endoprosthetic implant based on the determined size dimensions of the identified orthopedic element.

An exemplary system for determining the size of a component of an endoprosthetic implant to be surgically implanted into a patient, the system comprising: a tissue penetrating imaging machine; a first input image, the first input image taken by the tissue penetrating imaging machine from a first reference frame, the first image depicting a calibration jig; a second input image, the second input image taken by the tissue penetrating imaging machine from a second reference frame, the second reference frame being offset from the first reference frame, the second image depicting the calibration jig; a computational machine configured to run a deep learning network, wherein the deep learning network is configured to identify an orthopedic element to define an identified orthopedic element, and to map the identified orthopedic element to spatial data ascertained by the first input image and the second input image to thereby define determined size dimensions of the identified orthopedic element in three dimensional space; and a database, the database comprising a list of components of an endoprosthetic implant and associated component size dimensions for the components in the list of components of the endoprosthetic implant, wherein the computational machine is further configured to recommend a size of a component of an endoprosthetic implant based on the determined size dimensions of the identified orthopedic element in three dimensional space.

In an exemplary embodiment, the system further comprises a third input image, the third input image being taken by the tissue penetrating imaging machine from a third reference frame, the third image depicting the calibration jig.

In an exemplary embodiment, the identified orthopedic element is the internal geometry of a bone before or after reaming or before or after broaching.

In an exemplary embodiment, the computational machine is configured to run a best fit algorithm to select a recommended component of an endoprosthetic implant based on the determined size dimensions of the identified orthopedic element.

It is to be understood that the present invention is by no means limited to the particular constructions and method steps herein disclosed or shown in the drawings, but also comprises any modifications or equivalents within the scope of the claims known in the art. It will be appreciated by those skilled in the art that the devices and methods herein disclosed will find utility.

What is claimed is:

1. A system for ascertaining a position of an orthopedic element and a component of an endoprosthetic implant in space comprising:
   a tissue-penetrating imaging machine;
   a first two-dimensional input image, the first two-dimensional input image taken by the tissue penetrating imaging machine from a first reference frame, the first two-dimensional input image depicting a calibration jig;
   a second two-dimensional input image, the second two-dimensional input image taken by the tissue penetrating imaging machine from a second reference frame, the second reference frame being offset from the first reference frame at a first offset angle, the second two-dimensional input image depicting the calibration jig;
   a third two-dimensional input image, the third two-dimensional input image taken by the tissue penetrating imaging machine from a third reference frame, the third reference frame being offset from both the first reference frame and the second reference frame at a second offset angle, the third two-dimensional input image depicting the calibration jig, and the first two-dimensional input image, the second two dimensional input image, and the third two-dimensional input image comprising spatial data; and a computational machine configured to project the spatial data from the first two-dimensional input image, the second two-dimensional input image, and the third two-dimensional input image at the first offset angle and the second offset angle to define volume data, the computational machine further configured to run a deep learning network, wherein the deep learning network is configured to identify an orthopedic element from the volume data and a component of an endoprosthetic implant from the volume data to define an identified orthopedic element and an identified component of the endoprosthetic implant, and to map the identified orthopedic element and the identified component of the endoprosthetic implant to the spatial data ascertained by the first two-dimensional input image, the second two-dimensional input image, and the third two-dimensional input image to thereby determine the position of the identified orthopedic element and the identified component of the endoprosthetic implant in three-dimensional space, and wherein the computational machine is further configured to calculate an abduction angle of the identified component of the endoprosthetic implant or an anteversion angle of the identified component of the endoprosthetic implant.

2. The system of claim 1, wherein the deep learning network is further configured to identify multiple orthopedic elements and multiple components of the endoprosthetic implant to define multiple identified orthopedic elements and multiple identified components of the endoprosthetic implant.

3. The system of claim 2, wherein a first identified component of the multiple identified components of the endoprosthetic implant is an acetabular component of a hip endoprosthetic implant and wherein a second identified component of the multiple identified components of the endoprosthetic implant is a femoral component of a hip endoprosthetic implant.

4. The system of claim 1, wherein the identified component of the endoprosthetic implant is an acetabular shell and wherein the identified orthopedic element is a reamed acetabulum proximate to the acetabular shell.

5. The system of claim 1, wherein the identified component of the endoprosthetic implant is a femoral stem and wherein the identified orthopedic element is an intramedullary canal of a femur proximate to the femoral stem.

6. The system of claim 1, wherein the identified orthopedic element is modeled in three dimensions to define a modeled orthopedic element.

7. The system of claim 6, wherein the modeled orthopedic element is displayed on a display.

8. The system of claim 1, wherein the identified component of the endoprosthetic implant is modeled in three dimensions to define a modeled component of the endoprosthetic implant.

9. The system of claim 8, wherein the modeled component of the endoprosthetic implant is displayed on a display.

10. The system of claim 1, wherein the calculated abduction angle of the identified component of the endoprosthetic implant is displayed on a display.

11. The system of claim 1, wherein the calculated anteversion angle of the identified component of the endoprosthetic implant is displayed on a display.

12. A system for recommending a type of a component of an endoprosthetic implant to be surgically implanted into a patient, the system comprising:

a tissue penetrating imaging machine;

a first two-dimensional input image, the first two-dimensional input image taken by the tissue penetrating imaging machine from a first reference frame, the first two-dimensional image depicting a calibration jig;

a second two-dimensional input image, the second two-dimensional input image taken by the tissue penetrating imaging machine from a second reference frame, the second reference frame being offset from the first reference frame at a first offset angle, the second two-dimensional image depicting the calibration jig;

a third two-dimensional input image, the third two-dimensional input image taken by the tissue penetrating imaging machine from a third reference frame, the third reference frame being offset from both the first reference frame and the second reference frame at a second offset angle, the third two-dimensional input image depicting the calibration jig, and the first two-dimensional input image, the second two dimensional input image, and the third two-dimensional input image comprising spatial data;

a computational machine configured to project the spatial data from the first two-dimensional input image, the second two-dimensional input image, and the third two dimensional input image at the first offset angle and the second offset angle to define volume data, the computational machine further configured to run a deep learning network, wherein the deep learning network is configured to identify an orthopedic element from the volume data to define an identified orthopedic element from the volume data, and to map the identified orthopedic element to the spatial data ascertained by the first two dimensional input image, the second two-dimensional input image, and the third two-dimensional input image to thereby define determined size dimensions of the identified orthopedic element in three dimensional space; and a database, the database comprising a list of types of components of an endoprosthetic implant and a list of associated component size dimensions for each type of component in the list of types of components of the endoprosthetic implant, wherein the computational machine is further configured to select a recommended type of component of an endoprosthetic implant based on the determined size dimensions of the identified orthopedic element in three dimensional space.

13. The system of claim 12, wherein the identified orthopedic element is the internal geometry of a bone before or after reaming or before or after broaching.

14. The system of claim 13, wherein the computational machine is configured to run a best fit algorithm to select the recommended component of an endoprosthetic implant based on the determined size dimensions of the identified orthopedic element.

15. A system for determining the size of a component of an endoprosthetic implant to be surgically implanted into a patient, the system comprising:

a tissue penetrating imaging machine;

a first two-dimensional input image, the first two-dimensional input image taken by the tissue penetrating imaging machine from a first reference frame, the first two-dimensional image depicting a calibration jig;

a second two-dimensional input image, the second two-dimensional input image taken by the tissue penetrating imaging machine from a second reference frame, the second reference frame being offset from the first reference frame at a first offset angle, the second two-dimensional image depicting the calibration jig;

a third two-dimensional input image, the third two-dimensional input image taken by the tissue penetrating imaging machine from a third reference frame, the third reference frame being offset from both the first reference frame and the second reference frame at a second offset angle, the third two-dimensional input image depicting the calibration jig, and the first two-dimensional input image, the second two dimensional input image, and the third two-dimensional input image comprising spatial data;

a computational machine configured to project spatial data from the first two-dimensional input image, the second two-dimensional input image, and the third two-dimensional input image at the first offset angle and the second offset angle to define volume data, the computational machine further configured to run a deep learning network, wherein the deep learning network is configured to identify an orthopedic element from the volume data to define an identified orthopedic element, and to map the identified orthopedic element to the spatial data ascertained by the first two-dimensional input image, the second two-dimensional input image, and the third two-dimensional input image to thereby define determined size dimensions of the identified orthopedic element in three dimensional space; and a database, the database comprising a list of components of an endoprosthetic implant and a list of associated component size dimensions for each component in the list of components of the endoprosthetic implant, wherein the computational machine is further configured to recommend a size of a component of an endoprosthetic implant from the list of associated component size dimensions based on the determined size dimensions of the identified orthopedic element in three dimensional space.

16. The system of claim 15, wherein the identified orthopedic element is the internal geometry of a bone before or after reaming or before or after broaching.

17. The system of claim 15, wherein the computational machine is configured to run a best fit algorithm to select the recommended component of an endoprosthetic implant based on the determined size dimensions of the identified orthopedic element.

* * * * *